US012773539B2

(12) United States Patent
Fan et al.

(10) Patent No.: US 12,773,539 B2
(45) Date of Patent: Oct. 27, 2026

(54) SYSTEM AND METHOD FOR A VALVE

(71) Applicant: Medtronic PS Medical, Inc., Minneapolis, MN (US)

(72) Inventors: Cong Fan, Shanghai (CN); Yong Feng, Shanghai (CN); Jeff William Bertrand, Irvine, CA (US); Lori C. Speckman, Irvine, CA (US); Lawrence L. Hampton, Irvine, CA (US); Zhihua Luo, Shanghai (CN)

(73) Assignee: MEDTRONIC PS MEDICAL, INC., Minneapolis, MN (US)

( * ) Notice: Subject to any disclaimer, the term of this patent is extended or adjusted under 35 U.S.C. 154(b) by 682 days.

(21) Appl. No.: 18/027,869

(22) PCT Filed: Oct. 28, 2020

(86) PCT No.: PCT/CN2020/124432

§ 371 (c)(1),
(2) Date: Mar. 22, 2023

(87) PCT Pub. No.: WO2022/087898

PCT Pub. Date: May 5, 2022

(65) Prior Publication Data

US 2023/0338715 A1 Oct. 26, 2023

(51) Int. Cl.
*A61M 27/00* (2006.01)
*A61M 39/24* (2006.01)

(52) U.S. Cl.
CPC ..... *A61M 27/006* (2013.01); *A61M 2039/242* (2013.01); *A61M 2039/2433* (2013.01); *A61M 2039/248* (2013.01)

(58) Field of Classification Search
CPC .... A61M 2039/242; A61M 2039/2433; A61M 2039/246; A61M 2039/248; A61M 27/006; A61M 39/24; F16K 17/0406; F16K 17/06
See application file for complete search history.

(56) References Cited

U.S. PATENT DOCUMENTS

| | | | | |
|---|---|---|---|---|
| 5,368,556 A | | 11/1994 | Lecuyer | |
| 5,387,188 A | * | 2/1995 | Watson | A61M 27/006 604/8 |
| 5,637,083 A | | 6/1997 | Bertrand et al. | |
| 11,305,099 B1 | | 4/2022 | Mitchell et al. | |
| 11,752,315 B1 | | 9/2023 | Hakim | |
| 2002/0026139 A1 | | 2/2002 | Bertrand et al. | |

(Continued)

FOREIGN PATENT DOCUMENTS

| | | |
|---|---|---|
| CN | 202719220 U | 2/2013 |
| CN | 104870047 A | 8/2015 |

(Continued)

OTHER PUBLICATIONS

Chinese-Notice On Correction, corresponding to CN202080106419.9, Date of Dispatch: Jun. 13, 2023 (with English translation).

(Continued)

*Primary Examiner* — Kai H Weng
(74) *Attorney, Agent, or Firm* — Carter, DeLuca & Farrell, LLP

(57) ABSTRACT

A system includes a flow regulating system. The flow regulating system may assist in ensuring a selected pressure within an inlet volume. A flow regulator may be included in a shunt assembly (10).

13 Claims, 32 Drawing Sheets

(56) References Cited

U.S. PATENT DOCUMENTS

| | | | |
|---|---|---|---|
| 2005/0096579 | A1 | 5/2005 | Bertrand et al. |
| 2010/0010415 | A1 | 1/2010 | McCusker et al. |
| 2012/0046595 | A1 | 2/2012 | Wilson et al. |
| 2013/0085441 | A1 | 4/2013 | Aihara |
| 2013/0345646 | A1 | 12/2013 | Bertrand et al. |
| 2014/0207043 | A1 | 7/2014 | Anand et al. |
| 2014/0276348 | A1 | 9/2014 | Alan |
| 2019/0060621 | A1 | 2/2019 | Bertrand |
| 2019/0336736 | A1 | 11/2019 | Bertrand et al. |
| 2023/0330400 | A1 | 10/2023 | Fan et al. |
| 2023/0338715 | A1 | 10/2023 | Fan et al. |
| 2023/0347119 | A1 | 11/2023 | Fan et al. |

FOREIGN PATENT DOCUMENTS

| | | | |
|---|---|---|---|
| CN | 105358207 | A | 2/2016 |
| CN | 106122544 | A | 11/2016 |
| CN | 111032143 | A | 4/2020 |
| CN | 116723875 | A | 9/2023 |
| CN | 116723880 | A | 9/2023 |
| CN | 116801936 | A | 9/2023 |
| EP | 1007140 | B1 | 10/2003 |
| JP | 2006014936 | A | 1/2006 |
| WO | WO-2011136241 | A1 | 11/2011 |
| WO | 2013191766 | A1 | 12/2013 |
| WO | 2014144703 | A2 | 9/2014 |

OTHER PUBLICATIONS

International Search Report and Written Opinion regarding International Application No. PCT/CN2020/124432, mailed Jul. 26, 2021; ISA/CN.

International Search Report and Written Opinion regarding International Application No. PCT/CN2020/124429, mailed Jul. 26, 2021; ISA/CN.

Chinese-Notice On Correction, corresponding to CN202080106420.1, Date of Dispatch: Jun. 12, 2023 (with English translation).

Extended European Search Report for related European Application No. 20959059.5; dated: Jul. 23, 2024; 11 pages.

International Search Report and Written Opinion regarding International Application No. PCT/CN2020/124427, mailed Jul. 27, 2021, ISA: CN.

International Search Report and Written Opinion regarding International Application No. PCT/CN2020/124436, mailed Jul. 27, 2021; ISA/CN.

Extended European Search Report for related European Application No. 20959062.9; dated: Jul. 23, 2024; 11 pages.

China Notice and Search Report CN 202080106419.9, dated Nov. 29, 2025, 5 pp.

China Office Action CN 20208016419.9, dated Nov. 29, 2025, 20 pp.

* cited by examiner

Disclosure-1-5

SYSTEM AND METHOD FOR A VALVE

CROSS-REFERENCE TO RELATED APPLICATIONS

This application is a 371 U.S. National Phase of International Application No. PCT/CN2020/124432, filed on Oct. 28, 2020. This application includes subject matter similar to PCT applications POT/CN2020/124427, filed Oct. 28, 2020, PCT/CN2020/124429, filed Oct. 28, 2020, and PCT/CN2020/124436, filed Oct. 28, 2020. The entire disclosures of each of the above applications are incorporated herein by reference.

FIELD

The subject disclosure relates to a valve, and particularly to a valve assembly having an inlet and outlet catheter.

BACKGROUND

This section provides background information related to the present disclosure which is not necessarily prior art.

A subject, such as a human patient, may have a condition for which a treatment may be prescribed. For example, hydrocephalous may generally include an overproduction of cerebral fluid in the ventricles of the brain and/or an abnormal absorption or outflow of cerebral fluid from the brain. The condition, therefore, may cause an inappropriate or undesirable increase in volume of cerebral spinal fluid (CSF) within the ventricles in the brain and an increased pressure on the brain within the skull.

In various instances, a shunt may be implanted into the subject. The shunt may include an inflow catheter positioned within a ventricle of the brain and an outflow catheter positioned at a location remote from the brain. The excess cerebral spinal fluid may, therefore, flow from the ventricle to a selected location in the subject. The flow of the CSF from the ventricle through the inflow and outflow catheters may allow for an appropriate or selected volume of CSF within the brain to achieve a selected pressure on the brain within the skull. Maintaining a selected pressure within the ventricles, however, is desired.

SUMMARY

This section provides a general summary of the disclosure, and is not a comprehensive disclosure of its full scope or all of its features.

A catheter may be positioned in a selected portion of a subject, such as within a ventricle of a brain of a human subject. The catheter may include passages, such as bores, through a selected portion of a catheter. The catheter may further include an internal cannula or passage to allow flow of a selected material, such as a liquid, therethrough. In various embodiments, the catheter may allow for flow of cerebral spinal fluid (CSF). The catheter may be implanted as a part of a shunt system to shunt or drain CSF from a first location to a second location.

The shunt assembly may include the catheter positioned within the ventricle of the brain and a catheter positioned at a location remote from the ventricle of the brain. Positioned between the ventricle and the remote location may be a flow regulating system. The flow regulating system may include a valve assembly that is positioned in line with the catheters. The valve assembly may be used to regulate or select a pressure to be maintained within the ventricle.

In various embodiments the valve assembly may include an opening or breaking pressure. The breaking pressure would need to be achieved and/or exceeded to open the valve and allow fluid flow through the valve. The valve assembly may include various portions that allow for variation of the inlet pressure prior to opening the valve, as discussed further herein. The valve assembly, therefore, may be used to maintain a selected volume and/or a pressure in a ventricle.

The valve assembly may include a selected opening or breaking pressure. The opening pressure may be used to select a selected pressure to be maintained within the ventricle of the subject. Maintaining a selected pressure within the ventricle of a subject allows for maintaining a selected volume or pressure of fluid at an inlet location of the shunt assembly. For example, the ventricle may be selected to maintain a selected volume or pressure but allowing for flow of a fluid away from the ventricle when an excessive or selected threshold pressure has been reached.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
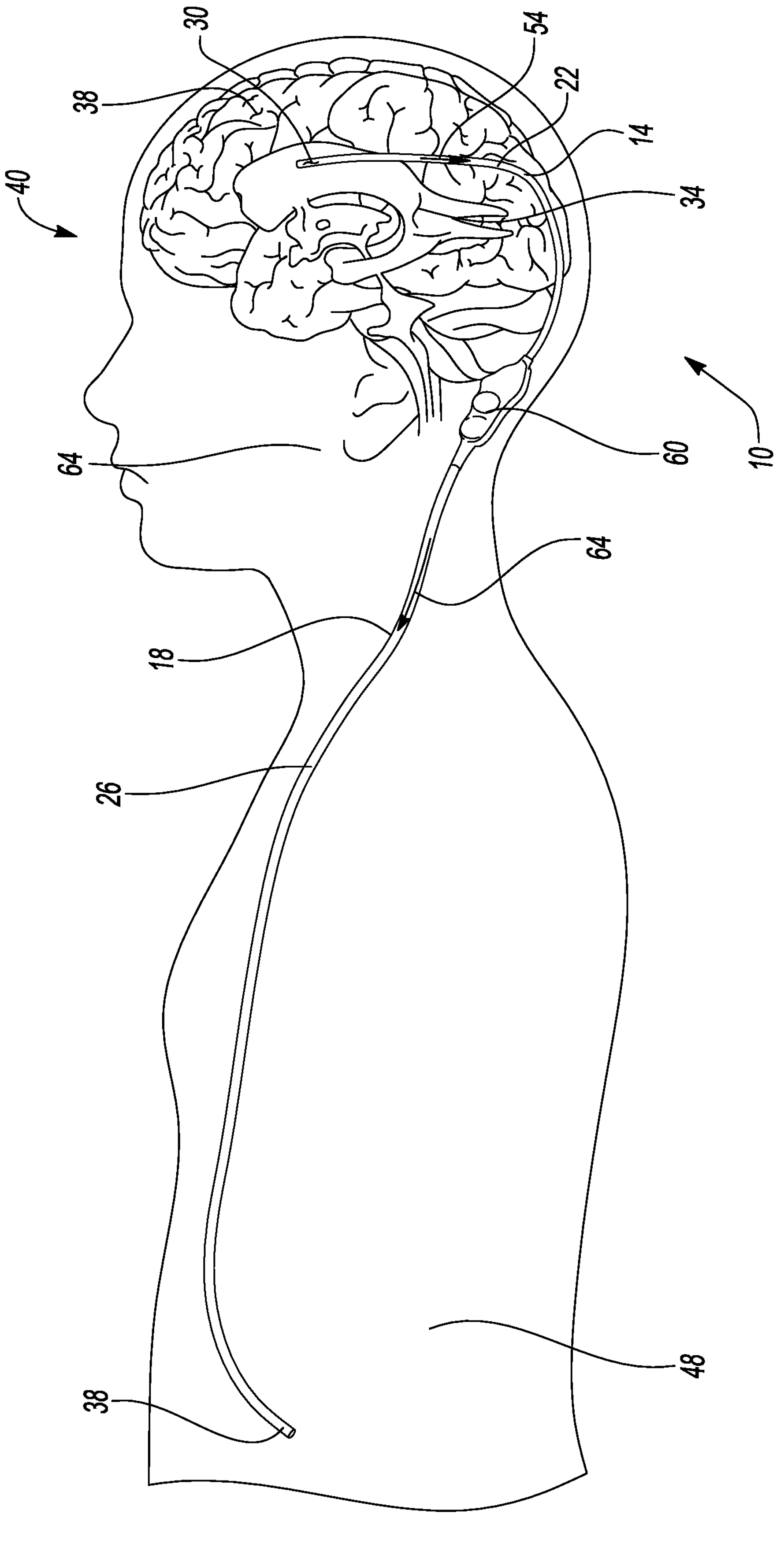
FIG. 1 is an environmental schematic view of a shunt and system positioned in a subject, according to various embodiments.

With initial reference to FIG. 1, a shunt system 10 is illustrated. The shunt system may include an inlet or first catheter 14 and an outlet or second catheter 18. The catheters, 14, 18 includes a member or wall structure that includes or defines an exterior surface 22, 26. The catheters 14, 18 may include a selected length or be formed along a long or longitudinal axis. In various embodiments, the catheter 14 may be provided as an inflow or inlet catheter or portion for the shunt assembly 10 as a hydrocephalous shunt. The hydrocephalous shunt may be configured, such as formed, assembled, and/or implanted to shunt cerebral spinal fluid (CSF) from a position near a first or inlet portion 30 of the catheter 14 in a ventricle 34 in a brain 38 of a subject 40 to a second or distal end 42 at a position remote or away from the inlet end or portion 30. The second our outlet end 38 may be in a selected portion of the subject 40, such as a peritoneum 48.

A fluid, such as a cerebral spinal fluid (CSF) may flow along the catheter 22 from ventricle 34 generally in the direction of arrow 50 toward the outlet end 38. As is generally understood by one skilled in the art, the inlet catheter 22 may be positioned (i.e. implanted) in the ventricle 34 to allow the fluid to be drained away from the ventricle 34. The inlet catheter 22 may be a part of the shunt system 10 that includes a selected flow control system, such as a valve assembly 60, according to various embodiments, as discussed further herein.

The valve assembly 60 may be implanted in the subject 40 in an appropriate position. In various embodiments, the valve assembly 60 may be implanted generally subdermal near an ear 64 of the subject 40, or any other appropriate location. It is understood that the inlet catheter 22 may be connected to the valve assembly 60. Thus, the inlet catheter 22 and the valve assembly 60 may both be implanted in the subject 40.

The subject disclosure includes an exemplary application for draining CSF in a subject. It is understood, however, that the valve assembly 60, according to various embodiments and/or portions thereof, may be used or implemented for alternative uses. For example, draining a selected fluid in any appropriate portion of a subject. Further, subjects may be living or non-living. For example, the valve assembly may be used for controlling flow or pressure from a first tank to a second tanks or drain.

The valve assembly 60 may be further connected to the outlet catheter 26. The outlet catheter 26 may extend from the valve assembly 60 to a selected location, such as the peritoneal cavity 48 of the subject 40. The inlet catheter 22, the valve assembly 60, and the outlet catheter 26 may generally be understood to be the shunt system 10, such as a hydrocephalus shunt system. The shunt system 10 may be entirely implanted in the subject 40.

The fluid may flow in the direction of arrow 54 through the inlet catheter 22 to the valve assembly 60. The fluid may then flow through the valve assembly 60 and through the outlet catheter 26 generally in the direction of arrow 64. The fluid may then drain or pass through the outlet catheter 26 into a peritoneal cavity 48, or any other appropriate location of the subject 40. It is understood that the outlet catheter 26 may be positioned within the subject 40 in an appropriate location to allow for draining of the CSF from the ventricle 34 to an appropriate location, such as one with high blood flow. Accordingly, as illustrated in FIG. 1, the inlet catheter 22, the valve assembly 60 and the outlet catheter 26 may be implanted or positioned in the subject 40 as a CSF shunt system.

With continuing reference to FIG. 1 and further reference to FIG. 2, FIG. 3, and FIG. 4, the valve assembly 60 is illustrated and will be described in greater detail. The valve assembly 60 may include an inlet end or portion 80 and an outlet end or portion 84. Each of the ends 80, 84 may include connection portions to connect to the respective catheters 22, 26. For example, an inlet barb 88 may engage the inlet catheter 22 and an outlet barb 92 may engage the outlet catheter 26. It is understood, however, that other appropriate connection mechanisms may be provided to connect the valve assembly 60 to the respective catheters 22, 26. Further, the first end or inlet end 80 may be connected or formed with a base member or base portion 94. The base portion 94 may provide a base for the valve assembly 60 and the various portions therein, as discussed further herein. The base 94 may be formed as a single piece with the inlet 80 and/or may be formed of separate pieces that are fixed together, such as with selected bonding systems including sonic welding, adhesives, and the like. Further, the base 94 may be positioned on a sheet or cover 98. In various embodiments, the valve assembly 60 may be positioned within the subject 40, as discussed above. The sheet 98 may assist in providing a barrier between the selected portion of the subject 40 and the valve assembly 60 and/or a firm or rigid base for the valve assembly 60. Further the sheet 98 may assist in maintaining the valve assembly 60 in a selected position relative to the subject 40.

The base 94 with the inlet 80 may define an inlet passage 100. The inlet passage 100 may extend to a first reservoir or directing area 104. The directing area 104 may direct a flow of the fluid generally in the direction of arrow 54 into a reservoir volume 108. The reservoir volume 108 may be reached by a passage 112 between the base 94 and a dome or cover 116. The dome or cover 116 may be formed of a selected material, such as silicon and/or selected polymers, and fixed to the base 94 and/or the sheet 98. The connection of the dome 116 to the base 94 and/or the sheet 98 may be in any appropriate manner, again, such as with adhesives, sonic welding, or the like. The formation of the dome 116 separate from the base 94 and/or the sheet 98 may assist in manufacturing or assembly of the valve assembly 60. One skilled in the art will, however, understand that the base 93, the sheet 98, and/or the dome 116 may be formed as a single member, according to various embodiments. Further, the dome 116 may be formed as one member, as illustrated in FIG. 4, and/or may be formed of a plurality of members that are fixed together.

The dome 116 may define, at least partially, the reservoir volume 108 relative to the base 94. Further, the dome 116 may cover or encapsulate a cassette assembly 120. The cassette assembly 120 may include an inlet 124 that may be reached via a passage 128 formed between the dome 116 and the cassette assembly 120. The cassette assembly 120 may include various portions that assist in forming a selected resistance or opening pressure, as discussed further herein. The cassette assembly 120, therefore, includes the inlet 124 and a cassette outlet 132.

The cassette outlet 132 may connect or pass to a flow limiting assembly 138. The flow limiting assembly 138 may also be referred to as a limiting or selective chamber assembly 138 including a chamber base 142 and a chamber case or cover 146. The flow limiter assembly 138 may include a chamber as included in a Delta® valve that is a valve that minimize overdrainage of fluid, such as cerebrospinal fluid (CSF). The chamber 142 with the case 146, therefore, assists in maintaining or limiting a selected outflow rate from the valve assembly 60 when the valve portion and the cassette assembly 120 is opened. For example, the flow limiting assembly 138 may limit an outflow from the valve assembly 60 to a selected amount that is dependent, at least in part, on a positive pressure at the inlet side of the flow limiting assembly 138 and a negative pressure at the outlet side of the flow limiting assembly 138. Generally, the flow limiting assembly 138 is to maintain the selected pressure of the opening of the valve assembly to the selected pressure, as discussed herein. The chamber 142, therefore, may include or define a limiting volume area 150 that is reached through an inlet 154 from the cassette outlet 132. The flow limiter assembly 138 may further include the outlet end 84. The Delta® valve is a valve sold by Medtronic, Inc. having a place of business in Minnesota, USA.

In various embodiments the flow limiter assembly 138 may be removably connected to the cassette assembly 120. For example, the chamber base 142 may include engaging edges or depressions 158. The engaging depressions 158 may be engaged by wings or fingers 162 of the cassette assembly 120. Therefore, the flow limiter assembly 138 may be removably connected from the cassette assembly 120, according to various embodiments.

The valve assembly 60 may further include the cassette assembly 120 held in the selected base or region 170 of the base 94. The cassette holding region 170 may include an outer wall or ridge 174 that assists in holding or fixing the cassette assembly 120 relative to the reservoir volume 108. Thus, the valve assembly 60 may be provided as the valve assembly unit or assembly as illustrated in FIG. 2, for implantation to the subject 40.

Briefly, therefore, the shunt assembly 10 may include the inlet catheter 22 positioned within the ventricle 34. The inlet catheter 22 will allow cerebral spinal fluid (CSF) to flow through the inlet catheter 22 to the inlet end 80 of the valve assembly 60. The CSF may flow through the inlet 80 and into the reservoir 108. Within the reservoir 108 the valve assembly 60 is substantially open to the ventricle 34. Accordingly, the pressure within the reservoir 108 may be substantially equal to the pressure within the ventricle 34.

The further passage 128, therefore, is also open to the reservoir 108. The cassette assembly 120 including a valve mechanism, as discussed herein, may open at a selected pressure that may be formed within the reservoir 108 due to the inflow from the ventricle 34 through the inlet catheter 22 of CSF or other selected fluid. At a selected pressure, the valve mechanism within the cassette assembly 120 may open and allow an outflow of the CSF through the cassette assembly 120 to the cassette assembly outlet 132. The flow limiter assembly 138 may assist in maintaining a selected outflow rate to the outlet catheter 26. Therefore, the reservoir 108 may be maintained with a selected volume and/or pressure and to ensure that the valve assembly 60 is not substantially drained of CSF. In various embodiments, the reservoir may be maintained substantially filled during use. Under various conditions, however, the reservoir 108 may not be filled and the percentage fill may be based on the amount of production of CSF and/or drainage rate. Further, the valve assembly may be included to maintain a selected pressure within the ventricle 34, such as about 0 centimeters (cm) of water to about 30 cm of water, including about 0 cm of water to about 20 cm of water, and further including not more than about 20 cm of water. One skilled in the art will understand that the cm of water is measured at standard temperature and pressure. Where the cm of water is defined in a column having a cross section area per the National Institute of Standards and Technology.

Figure 2:
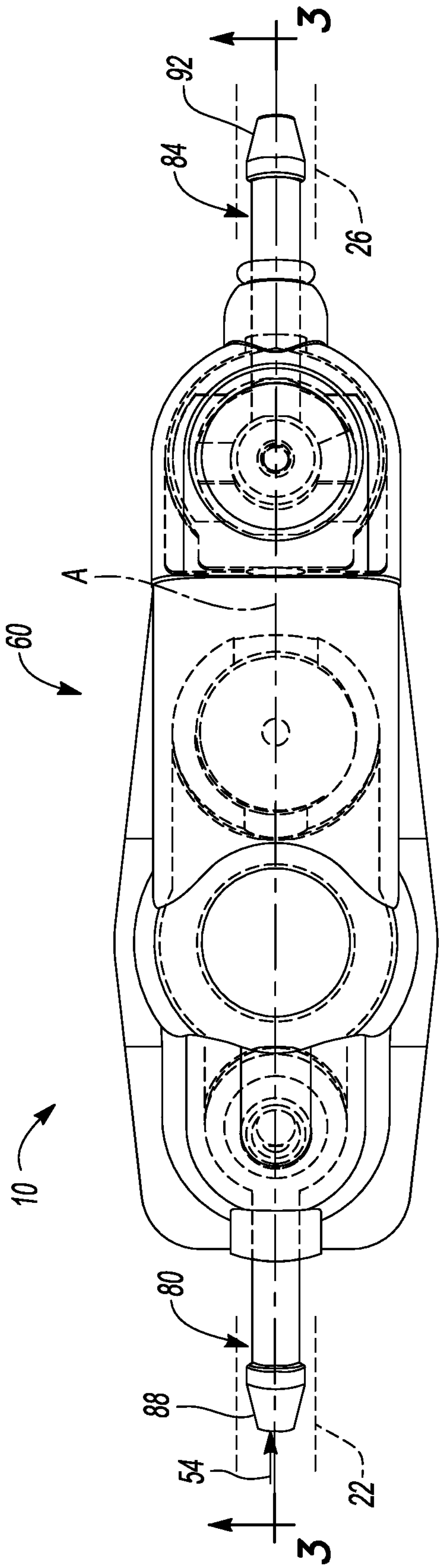
FIG. 2 is a top plan view of a valve assembly, according to various embodiments.
Figure 3:
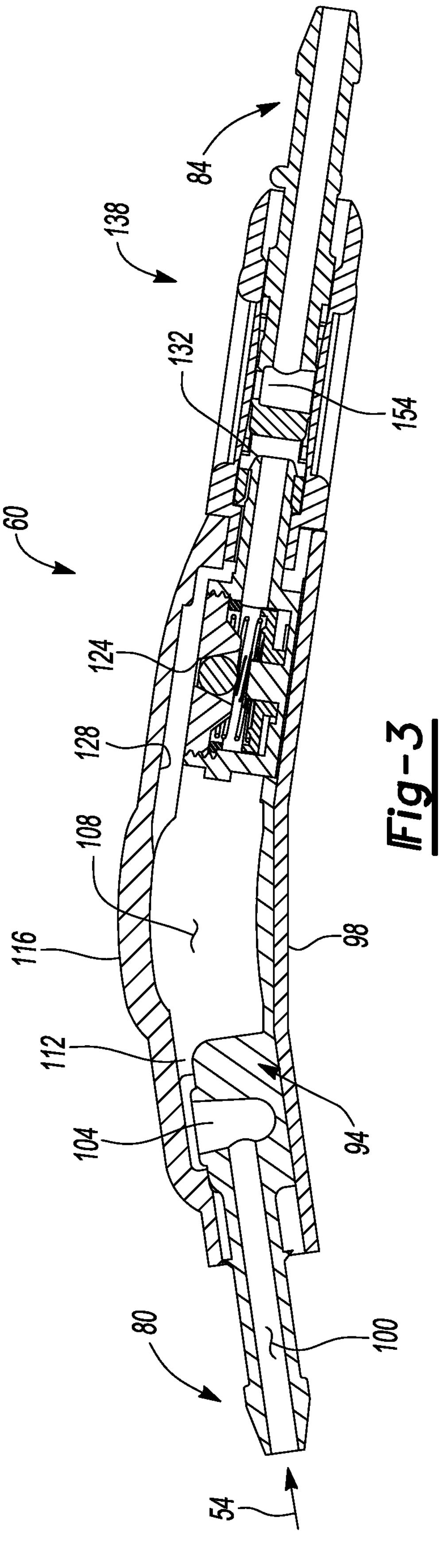
FIG. 3 is a cross-sectional view along line 3-3 of FIG. 2.
Figure 4:
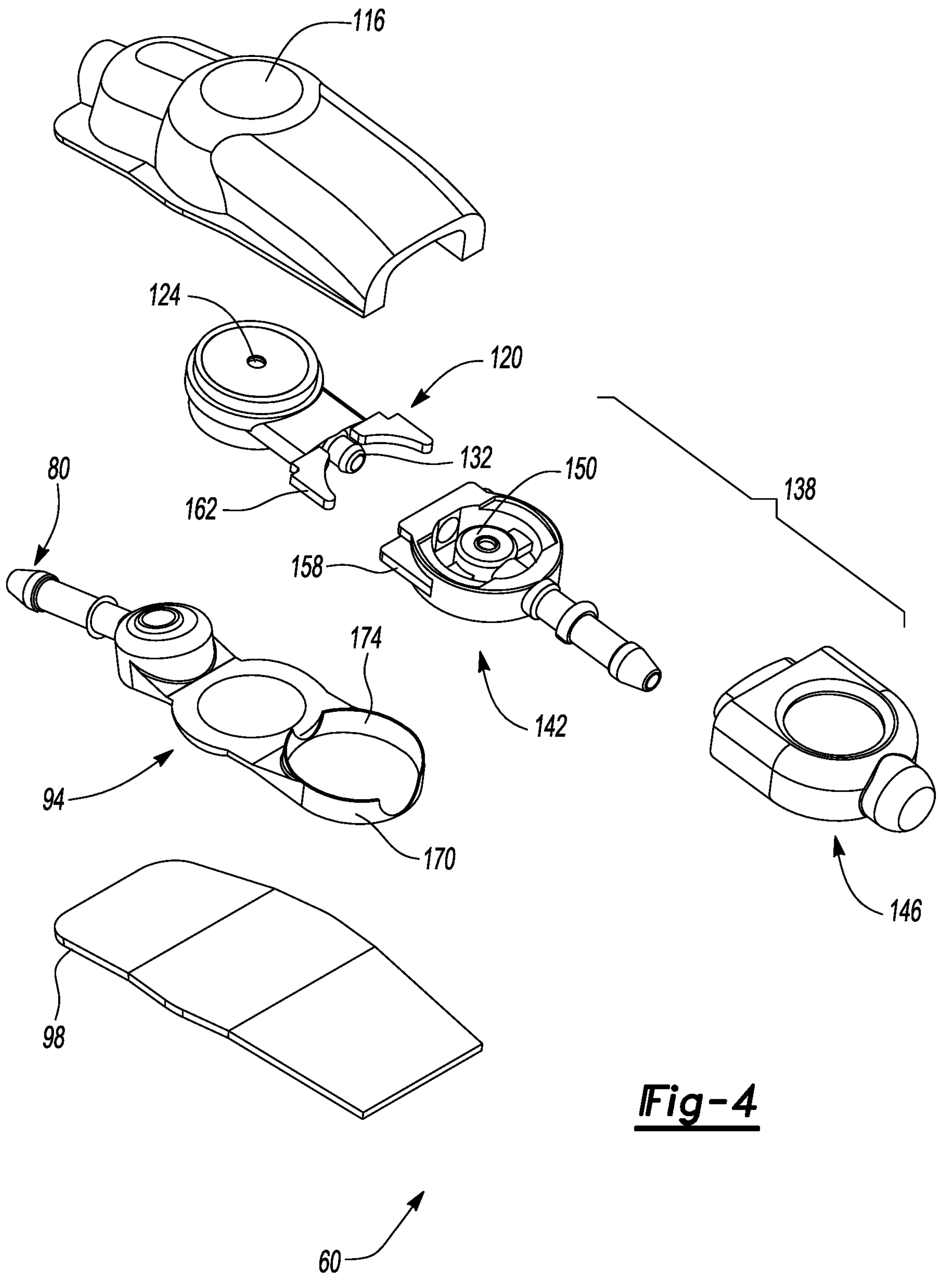
FIG. 4 is an exploded view of a valve assembly of FIG. 3.

With continuing reference to FIGS. 2-4, and additional reference to FIGS. 5A, 5B, 6, and 7, the cassette assembly 120, according to various embodiments, is illustrated in greater details. The cassette assembly 120 may generally include a cassette base or housing 190. The cassette housing 190 may include an outer wall 194 that defines an internal volume 196. Further, the wall 194 may define or form an internal thread 200. The cassette assembly 120 may further include a removable or selectively positioned cap 204 that includes an external thread 208 that may threadably engage the internal thread 200 of the cassette base 190. Accordingly, in various embodiments, the cap 204 may threadably engage the base 190 to assemble the cassette assembly 120. It is understood that other adjustable or selectively positionable connection may be provided such as a ratchet and pawl, or other appropriate connection mechanism. The threaded engagement may, however, allow for a selectable positioning of the cap 204, as discussed herein. It is understood that the cap 204 may also be fixed to the base 190 in any appropriate manner, such as with an adhesive, sonic welding, or the like, such as when the cap 204 is positioned at a selected position relative to the base 190. Thus, the cassette assembly 120 may be assembled in any appropriate manner. Generally the cap 204 defines or forms the inlet 124 of the cassette assembly 120.

Figure 7:
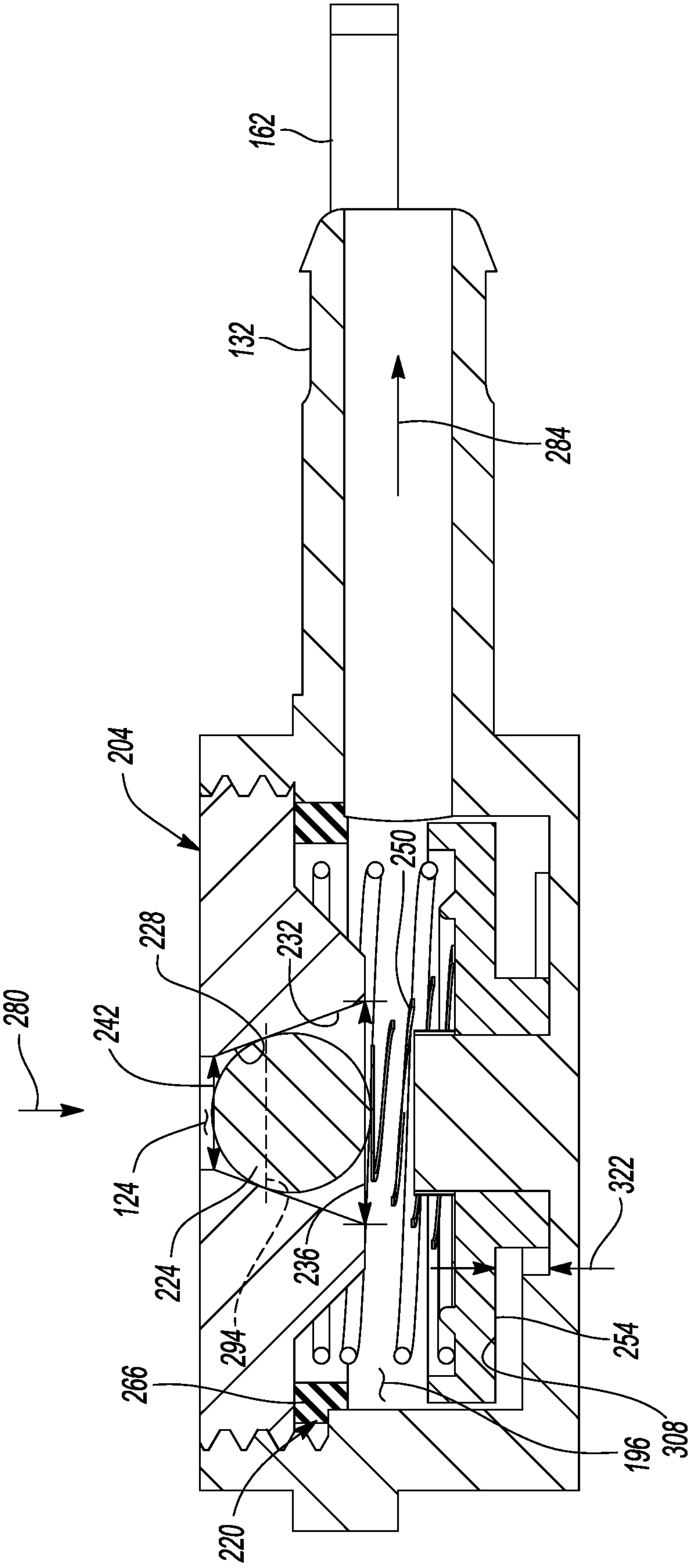
FIG. 7 is a cross-section view of an assembled cassette assembly taken along lines 7-7 of FIG. 5A.
Figure 8A:
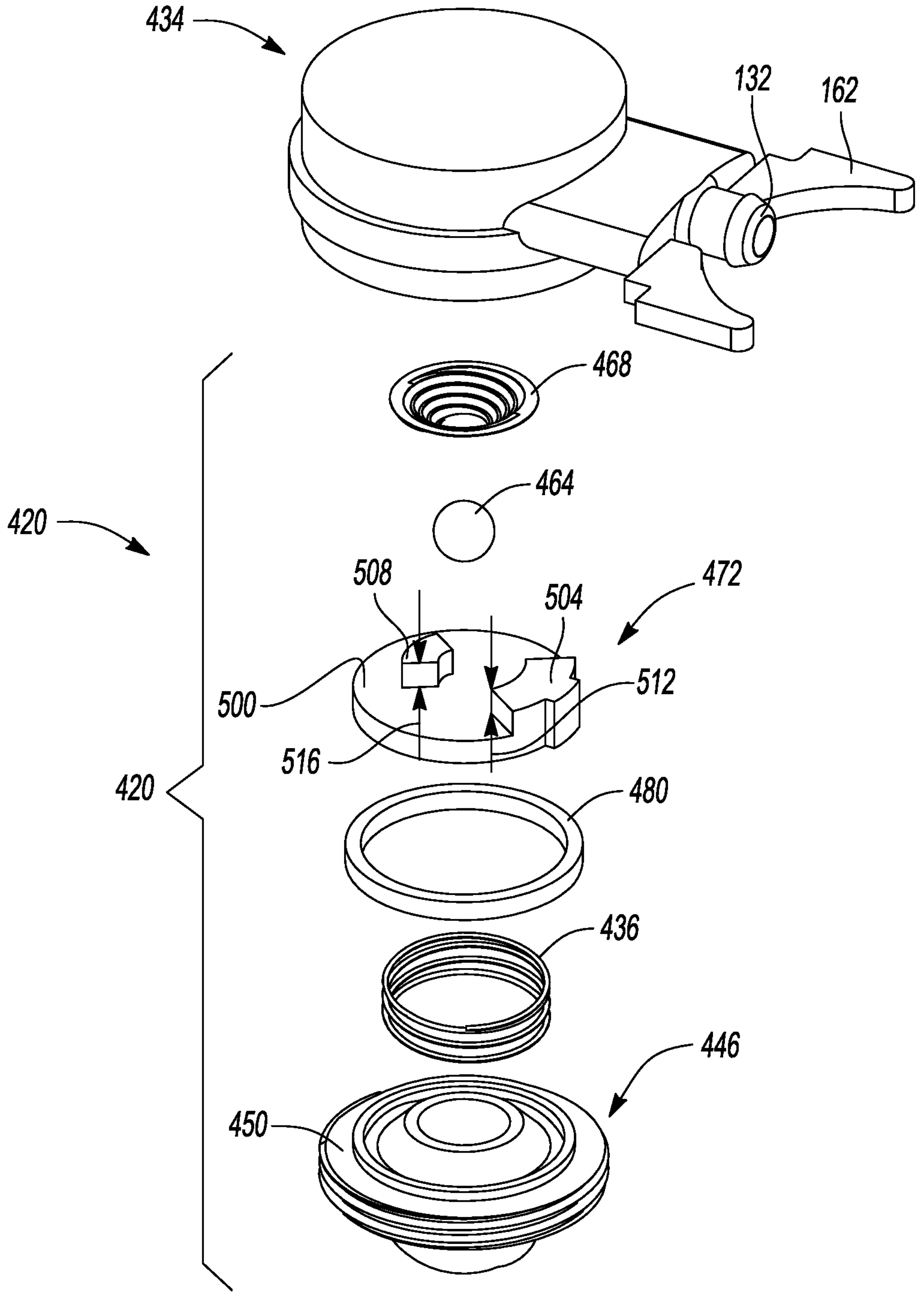
FIG. 8A is a first perspective exploded view of a cassette assembly, according to various embodiments.
Figure 8B:
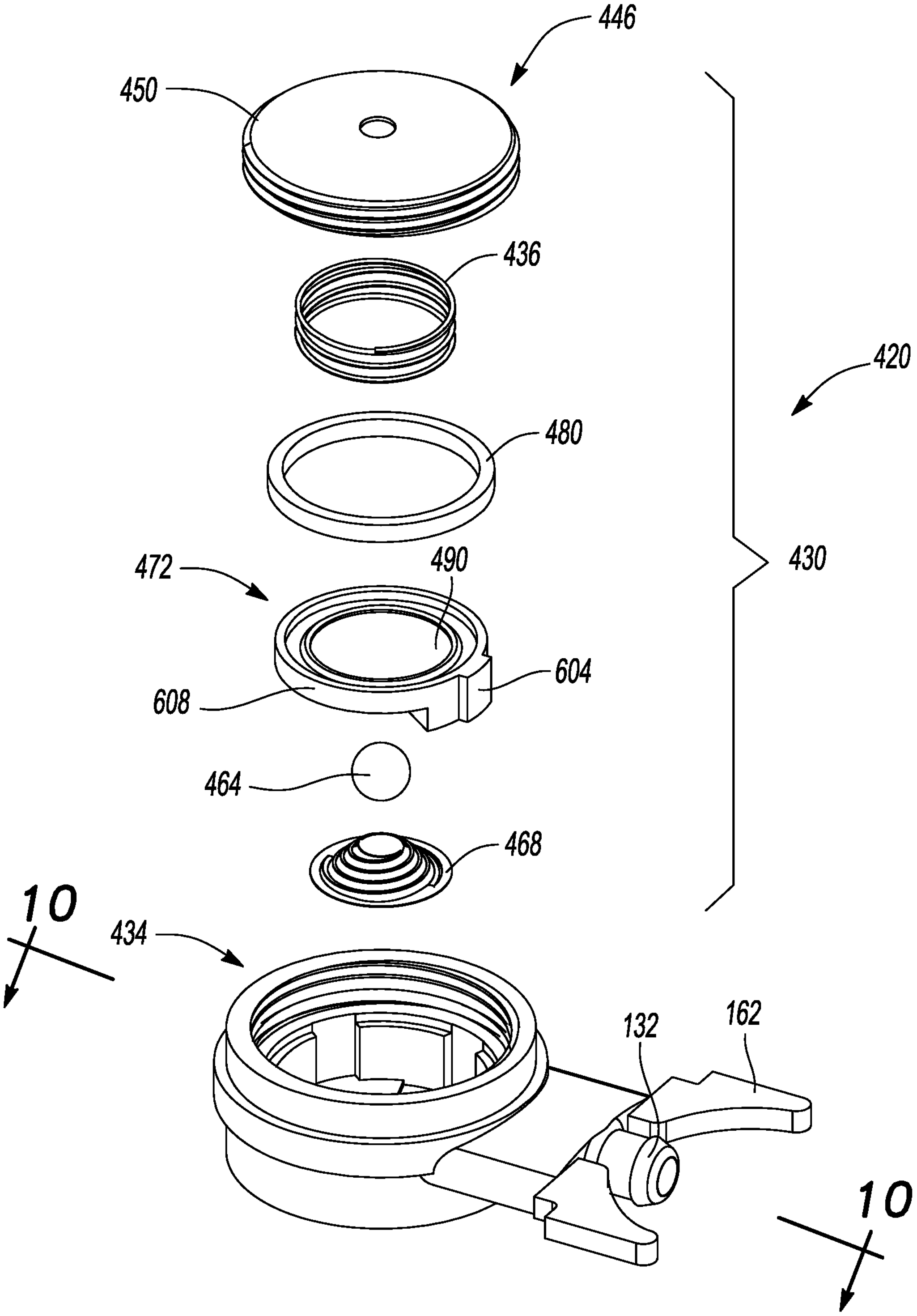
FIG. 8B is a second perspective exploded view of the cassette assembly of FIG. 8A.
Figure 9:
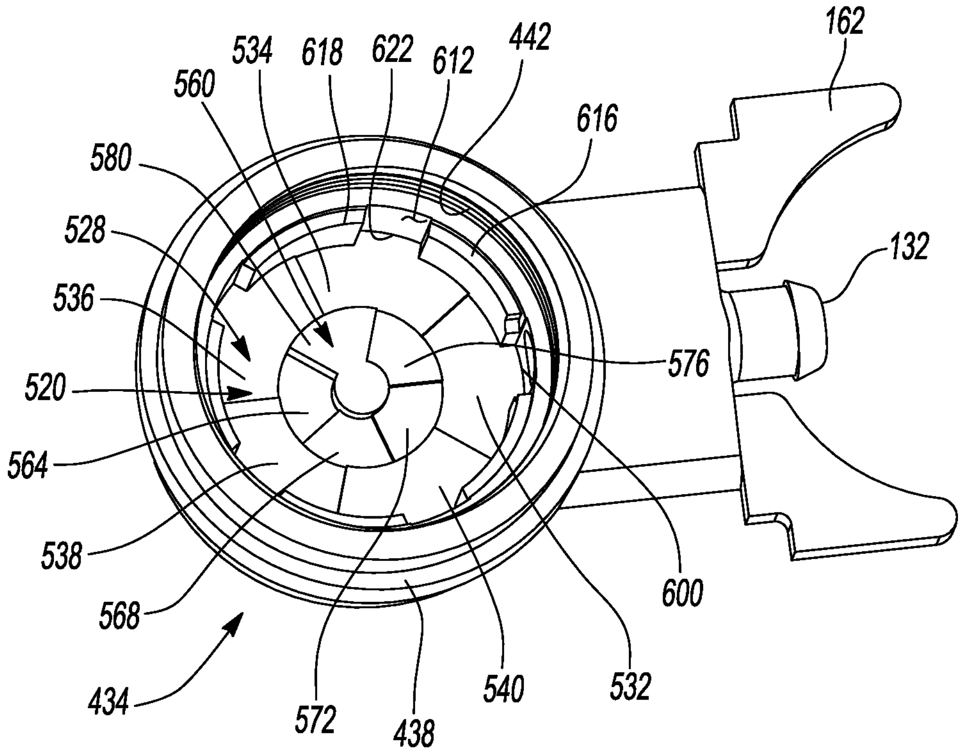
FIG. 9 is a detailed view of an interior of a cassette housing of the cassette assembly as illustrated in FIG. 8A.
Figure 10:
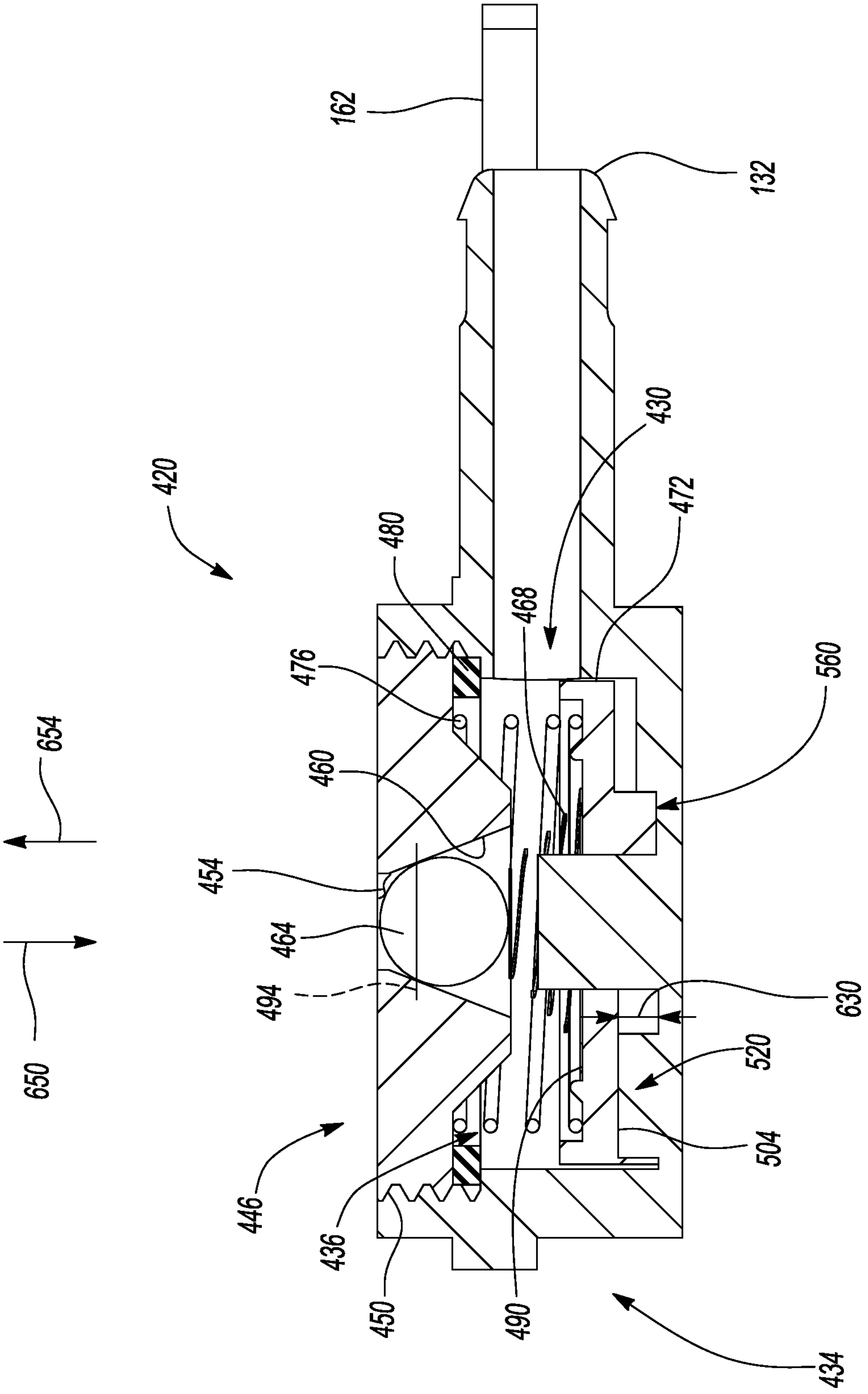
FIG. 10 is a cross-section view of an assembled cassette assembly taken along lines 10-10 of FIG. 8A.

The cassette body 190 may enclose at least a portion of a valve mechanism 220 of the valve assembly 60. The valve mechanism 220 may include a ball or movable seal portion 224 that may engage a seal portion or region 228 of the cap 204. As illustrated in FIG. 7, the cap 204 may define a cone or truncated cone that includes a tapered wall 232. The tapered wall or conical portion 232 may have a first diameter or dimension 236 that is greater than a diameter dimension 238 of the ball 224. The tapered wall 232 may include a second dimension 242 at a seal position that is less than the dimension 238 of the ball 224. Accordingly, when the ball 224 is pressed into the seal region 228, the ball 224 may seal the seal 228 by engaging the tapered wall 232. The ball 224 may be held or biased within the seal region 228 generally in the direction of arrow 246 by a biasing member 250. The biasing member may be a regulating member, as discussed herein, and may include a spring that may be referend to as a regulating or a biasing spring 250. The spring 250 may generally include a selected spring force that may be selected based upon a dimension of the cassette assembly 120 to ensure a selected force (e.g., a bias force) is applied to the ball 224 into the seal region 228. As discussed further herein, the seal spring 250 may be positioned between an adjustment member that may also be referred to as a rotor 254, which may operate as a pressure selecting member, and the ball 224. The rotor 254 may assist in selecting an opening (i.e., cracking) pressure of the cassette assembly 120 of the valve assembly 60, as discussed further herein. The opening or cracking pressure may be a threshold pressure at which the valve system, such as the valve mechanisms according to various embodiments, will open and allow a flow past the valve inlet.

The valve mechanism 220 further includes a return spring 258 that assists in maintaining the rotor 254 seated or positioned within the cassette housing 190. The return spring 258 may engage the cap 204 and the rotor 254 in a return spring trough or depression 262. The return spring 258, therefore, may selectively hold the rotor 254 within the cassette housing 190 when the cap 204 is engaged to the cassette housing 190.

Further the cassette assembly 120 may include a sealing member 266 that may be a washer or ring. The sealing member or washer 266 may be engaged between the cap 204 and the cassette housing 190. For example, as illustrated in FIG. 7, the sealing member 266 may be sealingly engaged to the cassette housing 190 when the cap 204 is engaged (e.g., with the respective threads) to the cassette housing 190. Thus, the internal volume 196 within the cassette housing 190 may be sealed or substantially closed relative to an external environment save through the inlet 124 and the cassette outlet 132.

Briefly, with reference to FIG. 7, at least a portion of the cassette assembly 120 may operate as the valve mechanism for the valve assembly 60. The inlet 124 is positioned within the valve assembly 60 on an inflow side or to allow inflow of fluid generally in the direction of arrow 280. When the pressure is great enough to overcome the force of the spring 250, the ball 224 may also generally move in the direction of arrow 280. The CSF may then flow through the inlet 124 and into the volume 196. The CSF may then flow through the outlet 132 generally in the direction of arrow 284. Thus, the CSF may enter the inlet 124 of the cassette assembly 120 and pass through the valve seal portion 228 due to movement of the ball 224 away from the valve seal 228. The CSF may flow through the cassette volume 196 and generally in the direction of arrow 284 out the cassette outlet 132.

The cassette assembly 120 may be set or assembled to include a selected opening pressure due to the positioning of the spring 250 and a spring force or opening force created by the spring 250 placed on the ball 224 in the seal 228. The force applied by the spring 250 against the ball 224 may be selected due to the position of a regulating base or surface 290 of the adjustment member 254 relative to the sealing region 228. As illustrated in FIG. 7, the sealing region 228 may seal against the ball 224 when the ball 224 is at a selected position. For example, the ball 224 may have a seal contacting edge or surface 294 that engages the sealing region 228. The position of the sealing edge 294 of the ball 224 may be selectively positioned at different heights relative to the spring engaging surface 290 of the rotor 254 to alter or change the force applied by the spring 250 to the ball 224.

Figure 5A:
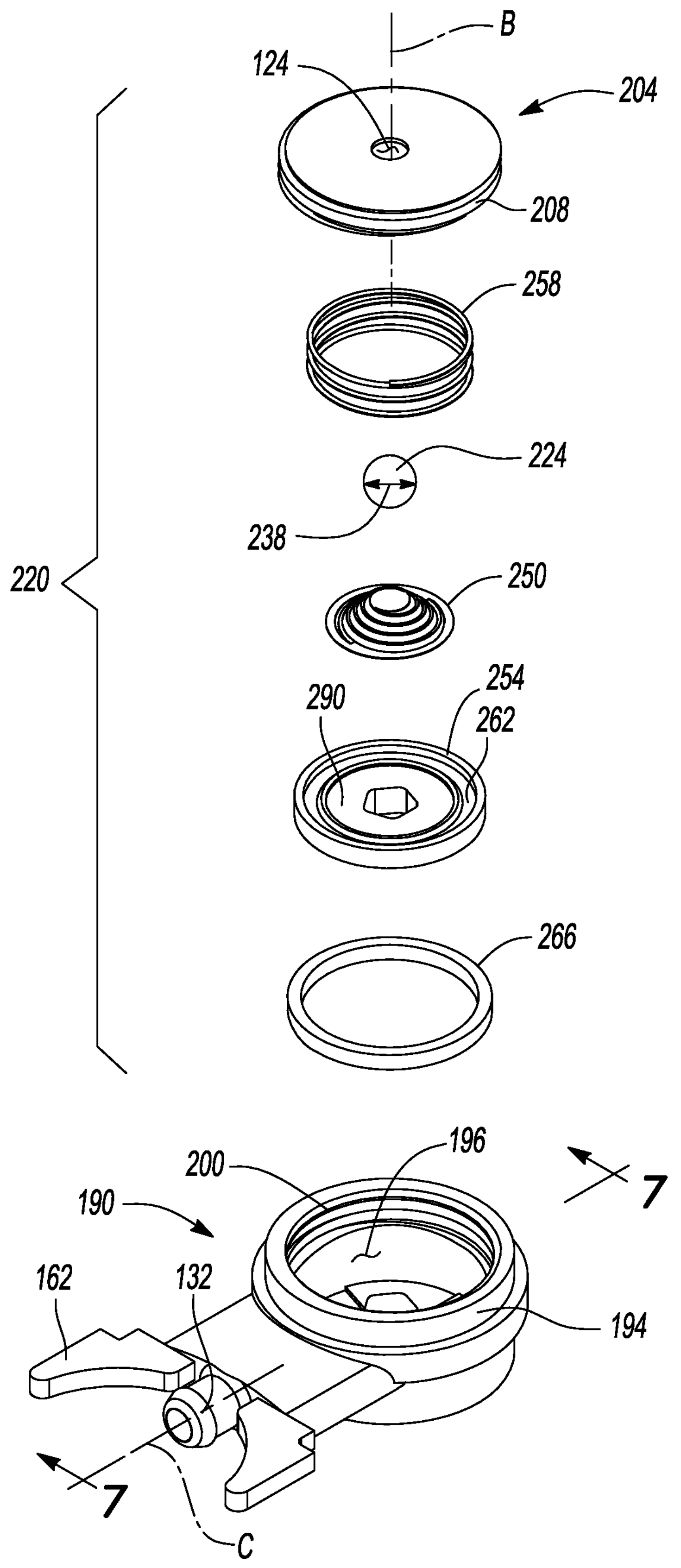
FIG. 5A is a first perspective exploded view of a cassette assembly, according to various embodiments.
Figure 5B:
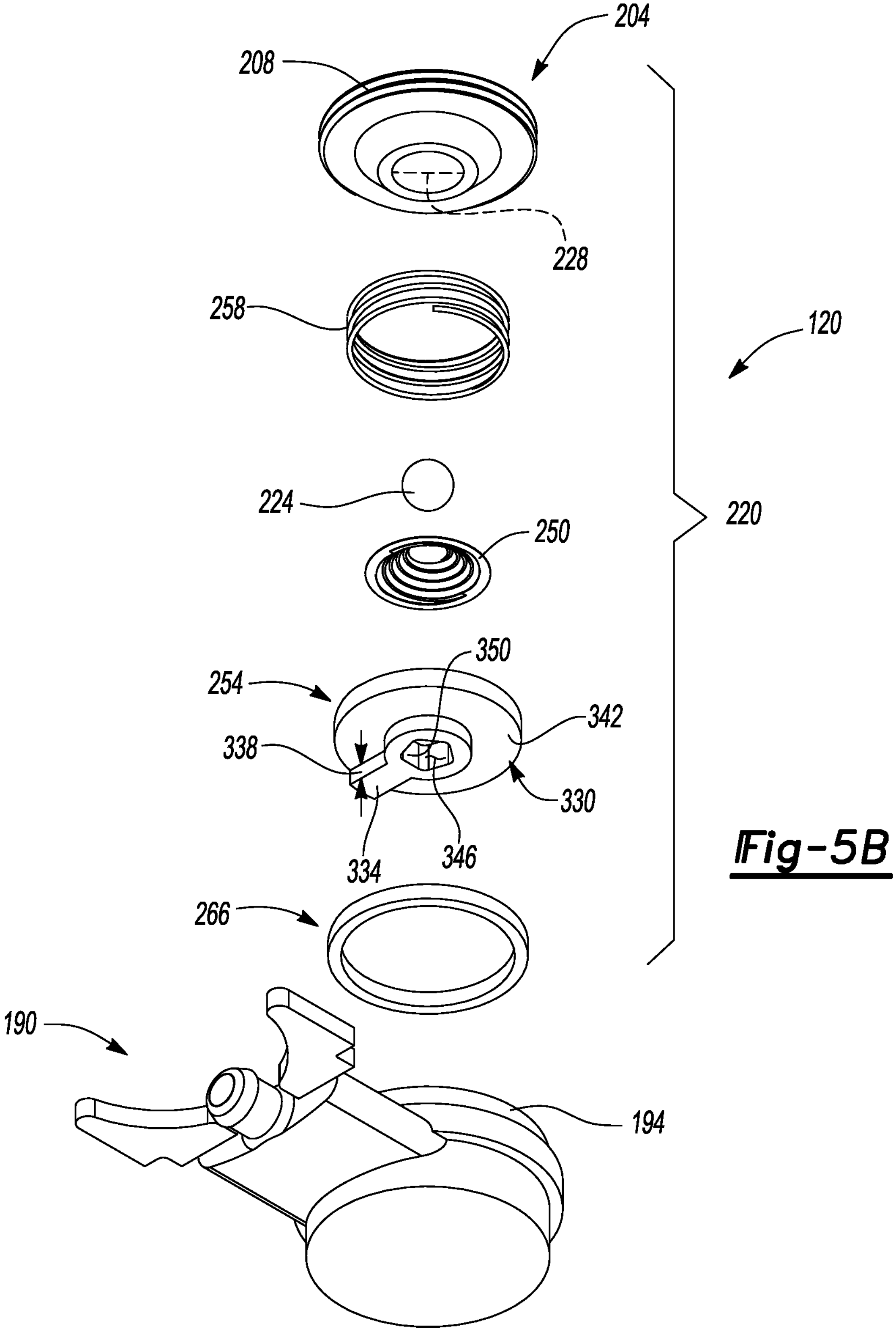
FIG. 5B is a second perspective exploded view of the cassette assembly of FIG. 5A.
Figure 6:
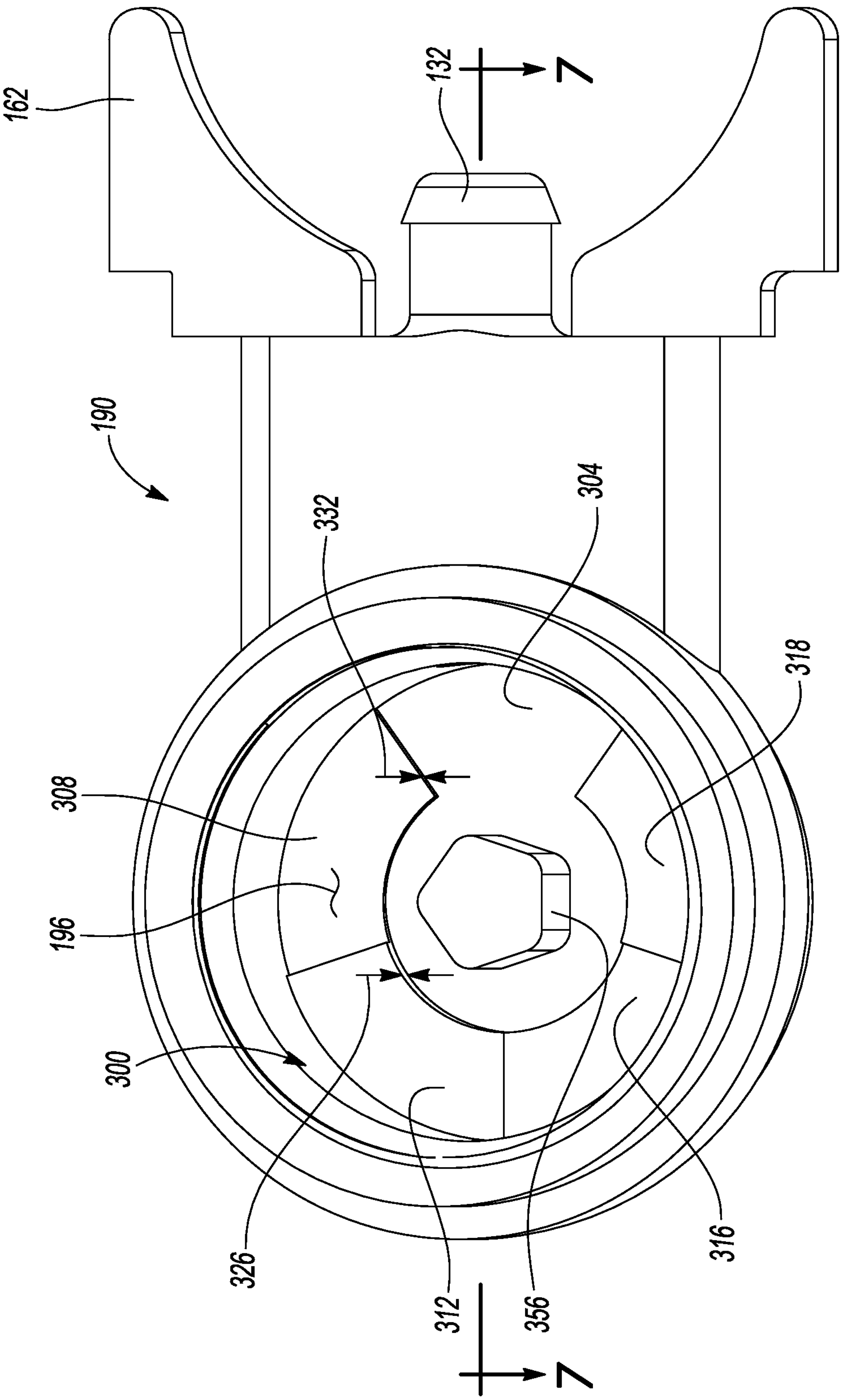
FIG. 6 is a detailed view of an interior of a cassette housing of the cassette assembly as illustrated in FIG. 5A, according to various embodiments.

With continuing reference to FIG. 5A and particular reference to FIG. 5B-7, the cassette assembly includes a height selecting region 300 (hereinafter referred to as "selecting region" 300). The selecting region 300 can include two or more surfaces (also referred to as steps) that have height variations within the cassette volume 196. A first height may be defined by a base or bottom floor surface 304 (hereinafter base 304). A second height may be defined by a first step 308 (hereinafter first step 308). A third height may be defined by a second step 312. Similarly a fourth and fifth height may be relatively defined by respective steps 316 and 318. As illustrated in FIG. 6, the first step 308 may have a height 322 relative to the base 304. The second step 312 may have a second height 326 relative to the base 304. Each of the base or the steps 304-318 may include different or varying height and the illustration of the two heights 322, 326 is merely for the clarity of the current discussion. In various embodiments, for example the step height may vary by about 0.001 millimeters (mm) to about 0.5 mm, including about 0.01 mm to about 0.3 mm, and further including about 0.1 mm to about 0.2 mm.

The rotor 254 may include an adjusting region 330. The bottom region 330 may include a foot or step engaging portion or surface 334. The step engaging portion 334 may extend a distance 338 from a bottom surface 342 of the rotor 254. The distance 338 may allow the foot or step engaging portion 334 to selectively and separately engaged one or more of the regions 304-318 of the height selecting region 300.

Further, the rotor 254 may include a central bore or passage 346. The bore 346 may include a selected shape, such as a polygon shape that may include a substantially pentagon shape, including a plurality of sides, such as a side 350. The cassette housing 190 may define or include a central peg or projection 354. The projection 354 may include a plurality of sides and generally have a selected crosssection or outer shape, such as a polygon shape that may include a pentagon shape. The projection 354, for example, may include a plurality of sides 356. Accordingly, the projection 354 may be engaged in the passage 346 of the rotor. As the projection 356 and the passage 346 are complementary in shape, the rotor 254 may be rotated to selected positions relative to the projection 356 and then rotationally held relative thereto due to the non-circular shape of the projection 354 engaging the recess or through bore 346. Thus, the rotor 254 may be rotationally positioned and held on the projection 354.

When the rotor 254 is rotationally positioned on the projection 356, the foot or positioning portion 334 engages one of the selected step or surface portions of the selecting region 300. For example, at a first position, the foot 334 may engage or contact the surface of the base 304. At a second position, the foot 334 may engage the first step 308 and be positioned the height 322 above the base 304.

As the foot 334 engages the step 308, the foot 334 is the distance 322 above the base 304. Accordingly, the distance 322 causes the rotor 254 to compress the spring 250 when the seal member 224 is positioned in the seal or seat 228. The compression of the spring 250 would apply additional force, due to the height 322, to the ball 224 into the sealing region 228. The biasing force, therefore, would be increased or altered relative to when the rotor 254 is positioned in the rotational position such that the foot 334 engages the base 304. Similarly, as the rotor 254 is rotated on to one of the other steps of the selecting region 300, the force or initial bias applied to the spring 250, and respectively, to the ball 224 would be altered.

The position of the rotor 254 on a selected one of the steps at the selecting region 300 selects an initial or opening force applied to move the ball 224 away from the sealing region 228. Accordingly, by positioning the rotor 254 to have the foot 334 engage a selected one of the steps or portions 304-318, the opening force required to move the ball 224 generally in the direction of the arrow 280 is altered such that the greater the height away from the base 304, the greater the force required to move the ball 224 out of the sealing position to the seal 228. Each of the steps may be selected to achieve a selected opening pressure such as about 0 cm of water to about 40 cm of water, including about 0 cm of water to about 20 cm of water, and include a pressure greater than about 20 cm of water.

Further, the cap 224 that is threadably engaged to the cassette housing 190 may also have a position of the cap 224 altered relative to the rotor 254. The cap 204 for example, may be loosened or moved generally in the direction of arrow 246 to decrease an opening pressure and/or move generally in the direction of arrow 280 to increase an opening pressure. A thread pitch of the threads 200, 208 may be selected to allow adjustments less than the adjustment caused by moving the rotor 254 to a different one of the steps in the adjustment region 300. Therefore, fine tuning or adjustments between the steps of the adjustment region 300 may be achieved by moving the cap, such as threading or unthreading the cap 204, relative to the rotor 254 in the alternative directions 246, 280.

Accordingly, the cassette assembly 120 may be set to a selected opening pressure, such as during manufacturing or at any appropriate time. For example, the valve mechanism 220 may be assembled into the cassette housing 190 at a selected opening pressure. The same valve mechanism may be set to a different opening pressure by positioning the rotor 254 at a different position on the adjustment region 300. Therefore, the valve mechanism 220 may be used to achieve a plurality of fixed or selected valve opening pressures with the same valve mechanism parts.

Additionally, or alternatively, a user may select a pressure at or during implantation from one of the plurality of possible opening pressures. The cassette assembly 120, may thereafter include the selected opening pressure without need for adjustment and/or ability to be adjusted after implantation without removal of the cassette assembly 120.

In various embodiments, the regulating spring 280 may be fixed to the rotor 254 in a selected manner such as with welding, adhesives, or the like. Similarly, the return spring 258 may also be fixed to the rotor 254 in a similar manner. It is understood, however, that the compressive forces of the cap 204 against the rotor 254 may selectively hold the respective springs 250, 258 in place during the use and operation of the cassette assembly 120.

Additionally, the rotor 254 may include a plurality of the step engaging portions 334 depending upon the configuration of the adjustment assembly 300. Further, in addition to and/or alternatively to the return spring 258, the rotor 254 may be bonded to the cassette housing 190 in a selected manner. For example, the rotor 254 may be adhered to the adjustment portion 300 with a selected adhesive that is biocompatible to hold the rotor 254 in a selected position relative to the cassette housing 190. The return spring 258 may be provided or not provided such that the rotor 254 is held in the cassette housing 190 without the return spring 258.

Further, the rotor 254 may include any selected passage shape that may be complementary to the projection 354 in the cassette housing 190. For example, the projection 354 may be hexagonal, octagonal, or any other appropriate shape. The shape may determine the number of selected adjustments at which the rotor 254 may be positioned relative to the cassette housing 190 and may also depend upon the number of variations provided in the adjustment region 300. Accordingly, the illustration of a pentagon shape of the projection 354 is merely exemplary and, for example, a hexagon shape may be provided along with six optional steps in the adjustment region 300.

With continuing reference to FIGS. 1-4 and additional reference to FIGS. 8A, 8B, 9, and 10, a cassette assembly 420 is illustrated. The cassette assembly 420 may be included with the valve assembly 60, as discussed above. The cassette assembly 420 may include portions similar to the cassette assembly 120, as discussed above. Accordingly, portions that are substantially identical to the cassette assembly 120, as discussed above, will not be discussed in greater detail here but may be discussed with reference to the cassette assembly 120. The cassette assembly 420 may include portions substantially identical to the cassette assembly 120, such as an outlet 132, an engagement or connection wings or projections 162. The cassette assembly 420, therefore, may be connected to or within the valve assembly 60. The cassette assembly 420, however, may include a valve mechanism 430 that may be positioned within the cassette housing 434 to selectively adjust or select an opening pressure in a manner as discussed further herein.

The cassette housing 434 may include an outer wall 438 that defines an internal thread 442, similar to that as discussed above. Accordingly, a cap 446 may also include an external thread 450 that may threadably engage the internal thread 442. The cap 446 may also include or define an inlet 454 similar to the inlet 124 as discussed above. Therefore, the cassette assembly 420 may be positioned in the valve assembly 60 in a similar manner as the cassette assembly 120, as discussed above.

Further, the cap 446 may define a seal region 460 that seals against or engages a sealing member, such as a ball 464. The ball 464 may be biased into the sealing region 460 with a biasing member 468, which may be a pressure regulating spring, similar to the spring 250 as discussed above. The valve mechanism 430 may further include an adjustment member 472, which may also be referred to as a rotor 472. The adjustment member 472 may selectively provide a selectable or selected position of the regulating spring 468 within the cassette housing 434. As discussed further herein, the rotor 472 may be positioned within the cassette housing 434 to assist in selecting an opening pressure of the cassette assembly 420. Further, a return spring 476 may be provided to assist in holding the rotor 472 within the cassette housing 434. As discussed above, however, the rotor 472 may also be fixed within the cassette housing 434, such as with an adhesive or similar mechanism. Further, the valve assembly 430 may include a sealing member 480, such as a washer or O-ring.

As discussed above, the sealing member 464 may be a sphere or ball and may be positioned within the sealing region 460 of the cap 446. The regulating spring 468 may bias the ball 464 against the sealing region 460. An upper regulating surface 490 of the rotor 472 that contacts or engages the spring 468 may be moved within the cassette housing 434 to a selected height such that the regulating surface 490 is positioned a selected height from the sealing position 494 of the ball 464 within the seal 460.

The rotor 472 may have a bottom or second surface 500 that is opposed or opposite the spring engaging surface 490. The rotor 472 may further include one or more projections, such as a first outer projection 504 and a second inner projection 508. The two projections 504, 508 may project a selected distance 512, 516 from the bottom surface 500. In various embodiments the distances 510, 516 may be identical. In various embodiments, however, the distances 512, 516 may be different.

The projections 504, 508 engage a selecting mechanism or area 520 within the cassette housing 434. The selection area 520 may be similar to the selection area 300, as discussed above. The selection area 520, however, will be discussed further herein. It is understood, however, that the selected area 300 may include various portions of the selection area 520 and vice versa.

The selection area 520 may include an outer or first set of selection regions 528. As discussed above, the selection region 528 may include a lowest or floor position 532 and a plurality of steps each raised a selected distance relative to each other and the base or floor 532. Accordingly, the outer steps or selection region 528 may include the base or floor 532 and four steps of varying heights or upper surfaces having distance of varying distance relative to the base 532. The steps or selection regions 532-540 allow for positioning the rotor 472 at various heights relative to the cap or the sealing region 494 similar to the alternative distances discussed above.

The selection area 520 may further include an inner selection area 560. The inner selection area 560 may also include a plurality of selection regions 564, 568, 572, 576, and 580. The individual inner selection portions 564-580 of the inner selection area 560 may also differ in height from one another similar to the outer selection area 520.

The outer selection area 520 may cooperate with the outer projection 504 and the inner selection area 560 may cooperated with the inner selection projection 508 of the rotor 472. Therefore, the rotor 472 may engage with the two projections 504, 508 two different selection areas 520, 560, respectively. This may allow for the rotor 472 to be rotationally fixed relative to the housing 434 in a manner greater than the single projection 334 of the rotor 254 engaging the single selection ring or portion 300 of the cassette 120 discussed above.

Further, the rotor 472 may be defined or formed with a closed surface and not include a passage to engage a projection of the cassette housing 434. In addition to the selection areas 520, 560, the cassette housing 434 may further include a rotational engagement or fixation region 600. The rotational fixation region 600 may also be referred to a rotor guide or indicator guide to engage an indicator or radial projection 604 of the rotor 472. The radial projection or indicator 604 may radially extend from an outer wall 608 of the rotor 472. The indicator 604 may be received or engage a passage or slot 612 defined between two inwardly projecting walls or projections 616, 618. The inwardly projecting walls 616, 618 may project a selected distance from an internal surface 622 of the cassette housing 434. Accordingly, the indicator guide or slot 612 may engage the indicator 604 to rotationally hold or assist in rotationally holding the rotor 472 relative to the cassette housing 434. In this way, the rotor 472 may be rotationally fixed or held within the cassette housing 434 with a plurality of mechanisms including the height selection portions 520, 560, engaging the respective projections 504, 508 of the rotor 472 and the indicator 604 be engaged in one of a plurality of slots 612 of the indicator guide portion 600. Accordingly, it is understood that the indicator guide 600 may include a plurality of the slots 612 that may aligned with the indicator 604 at each of the different selection regions of the selection portions 520, 560.

The cassette assembly 420 including the rotor 472 may selectively bias the sealing ball or member 464 into the sealing region 494. As exemplary illustrated, the outer projection 520 may include a selected height 630 relative to the base or lowest portion 532. The inner region 560 may include a similar or equivalent height. Accordingly, the inner and outer projections 508, 504, respectively, may respectively engage a selected one of the regions of the selection regions 520, 560 to position the spring engaging surface 490 at a selected distance from the sealing region 494 of the sealing portion 460. As discussed above by varying the distance of the surface 490 relative to the sealing region 494 alters a compression, and therefore the biasing force, of the spring. Thus, the force required to move the ball 464 away from the sealing area 460 generally in the direction of arrow 650 may be altered or selected.

As discussed above, the selection regions 520, 560 may be used to adjust the rotor 472 relative to the sealed position 494 in the seal 460. In addition and/or alternatively thereto, the cap 446 may be rotated through the interaction of the external threads 450 and the internal threads 442 to move the cap 446 either in the direction of the arrow 650 and/or in the direction of arrow 654 to adjust the force applied to the seal member 464. As discussed above, the thread pitch of the threads 450, 442 may be selected to allow for an adjustment of a position of the seal position 494 relative to the rotor 472 that is less than the height of the respective steps in the selection regions 520, 560, similar to that discussed above in the cassette assembly 120. Therefore, the cassette assembly 420 may also be used to select an opening pressure of the valve mechanism 430 within the cassette assembly 420, similar to the selection within the cassette assembly 120, as discussed above, but with the additions of variations as discussed above.

Turning reference to FIGS. 11A, 11B, 12, and 13, a cassette assembly 720 is illustrated and will be described further herein. The cassette assembly 720 may include various portions similar to those as discussed above, and details of the similar or identical portions will not be repeated in detail herein, however, reference to the prior discussion may be made. Accordingly, it is understood that various portions of the cassette assembly 720 may be similar or exchanged with the portions as described above and may be used in addition and/or alternatively thereto and vice versa.

The cassette assembly 720 may include a cassette housing 724, similar to the cassette housing as discussed above, such as the cassette housing 190 of the cassette assembly 120. The cassette housing 720 may include an external or outer wall 728 and may define an internal thread 732, again similar to that as discussed above. The cassette assembly 720 may further include a cap 736 which may define or include an external thread 740. Formed through the cap 736 may be an inlet 744 similar to the inlet 124 of the cassette assembly 120. Accordingly, the cassette assembly 720 may include the cap member 736 that may be engaged to the cassette housing 724 and define an internal volume or portion 748. The cassette assembly 720, such as in the cassette housing 724, may further include the outlet 132 and the connection portions 162. Thus, the cassette assembly 720 may include portions similar to those as discussed above, and including various portions as further discussed herein.

The cassette assembly 720 may further include a valve mechanism 760. The valve mechanism 760 may include various portions, similar to those as discussed above. A rotor 764 may be included in the valve mechanism 760 that includes a spring seat surface 768 that may engage a biasing member, such as a regulating spring 772. The regulating spring 772 may engage or be placed on the surface 768 and further against a valve or sealing member, such as a valve ball 776. The valve sealing member 776 may engage a seal portion or region 780 defined by the cap 736, similar to the seal regions as discussed above. The ball 776 may include an outer dimension that engages the seal region 780 in a sealed or closed configuration at a seal position 784. As discussed above, the regulating spring 772 may bias the sealing ball 776 against the sealing surface 780, generally in the direction of arrow 790.

The valve mechanism 760 may further include a return spring 794 that may be engaged by the cap 736 to assist in holding the rotor 764 in a selected position within the cassette housing 724. Further a seal member 798, such as a washer or O-ring may be positioned between the cap 736 and the cassette housing 724 to assist in maintaining or creating a seal between the cap 736 and the cassette housing 724 to seal or substantially close the internal volume 748 within the cassette assembly 720.

Figure 11A:
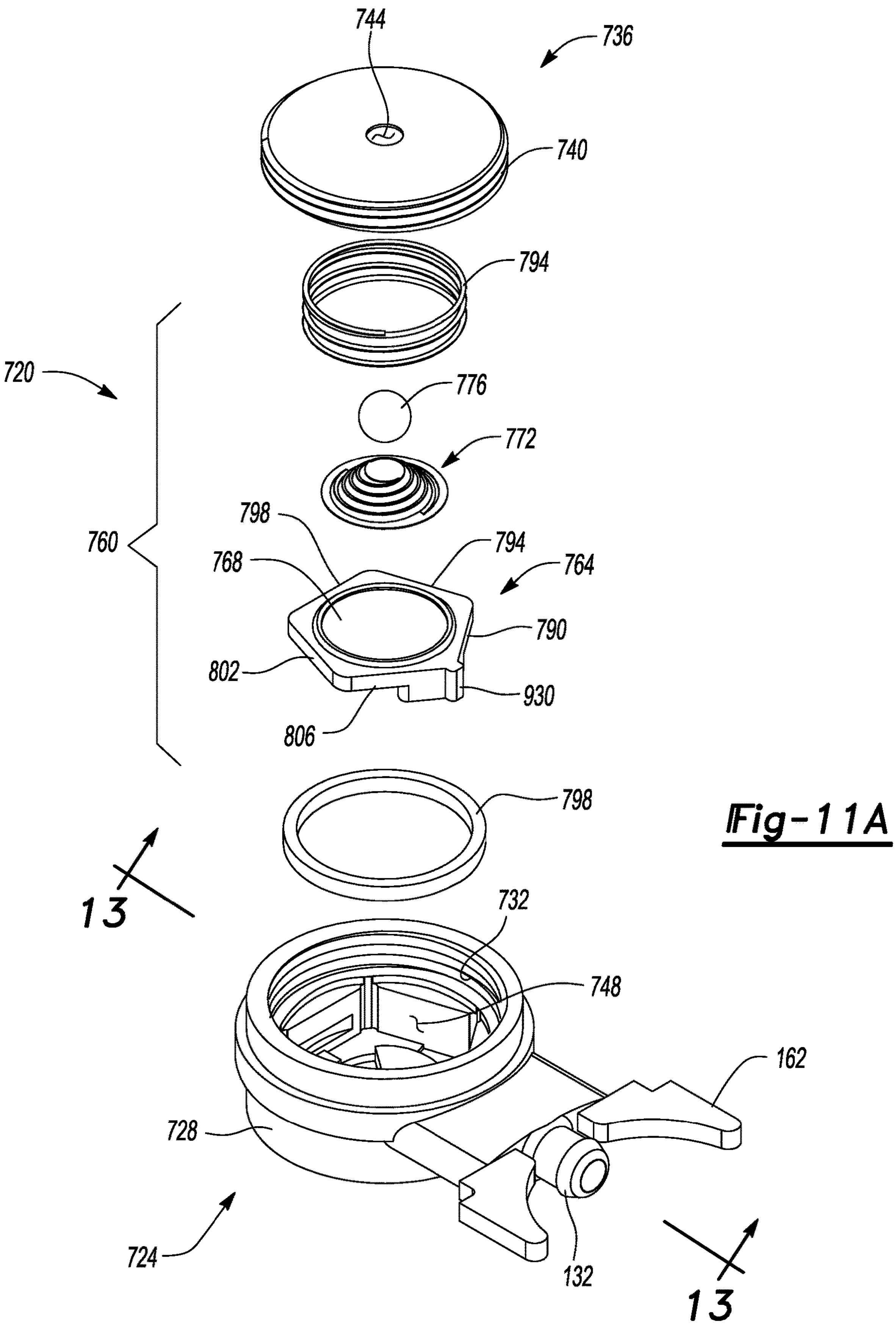
FIG. 11A is a first perspective exploded view of a cassette assembly, according to various embodiments.
Figure 11B:
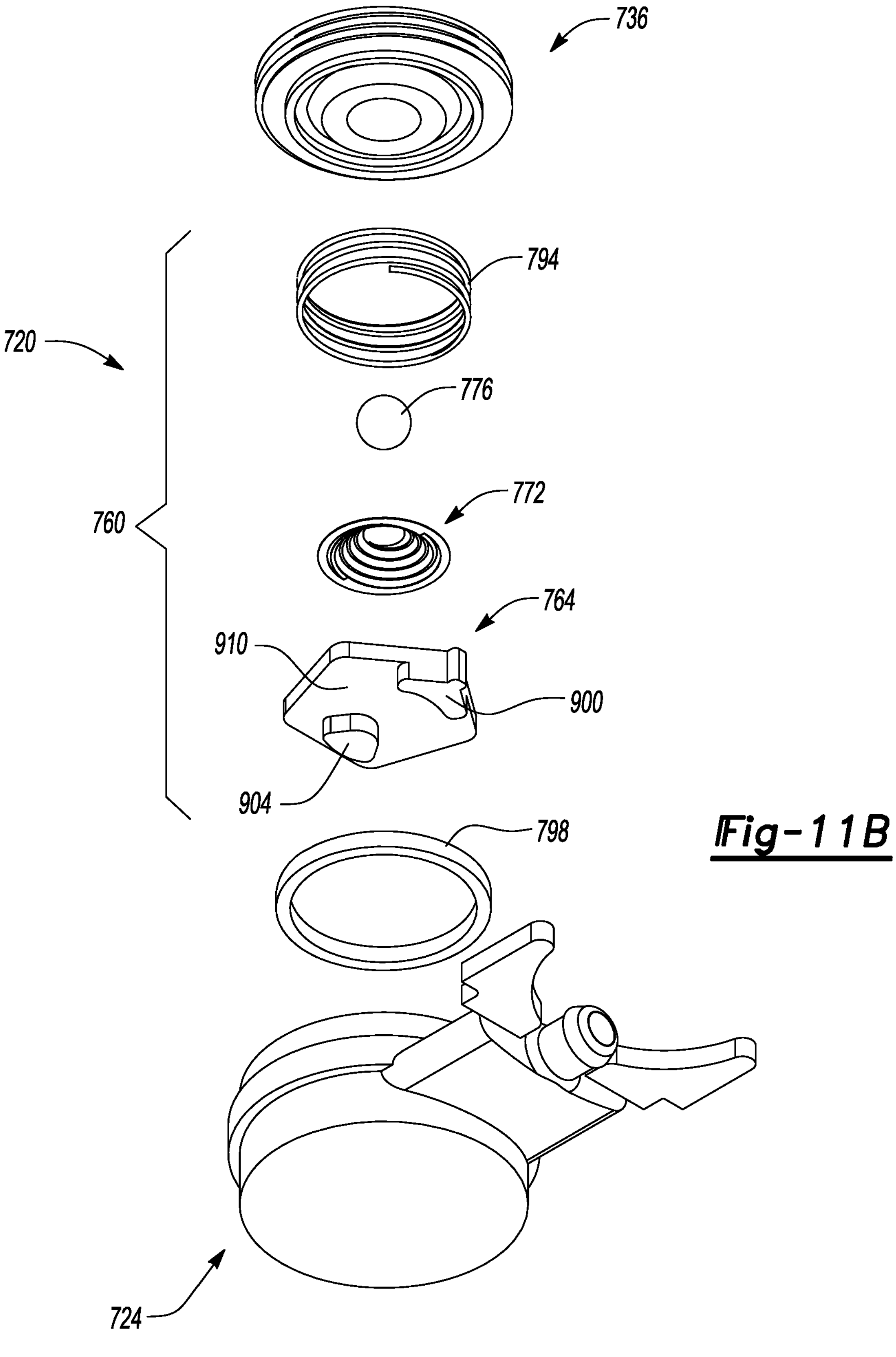
FIG. 11B is a second perspective view of an exploded cassette assembly of FIG. 11A.
Figure 12:
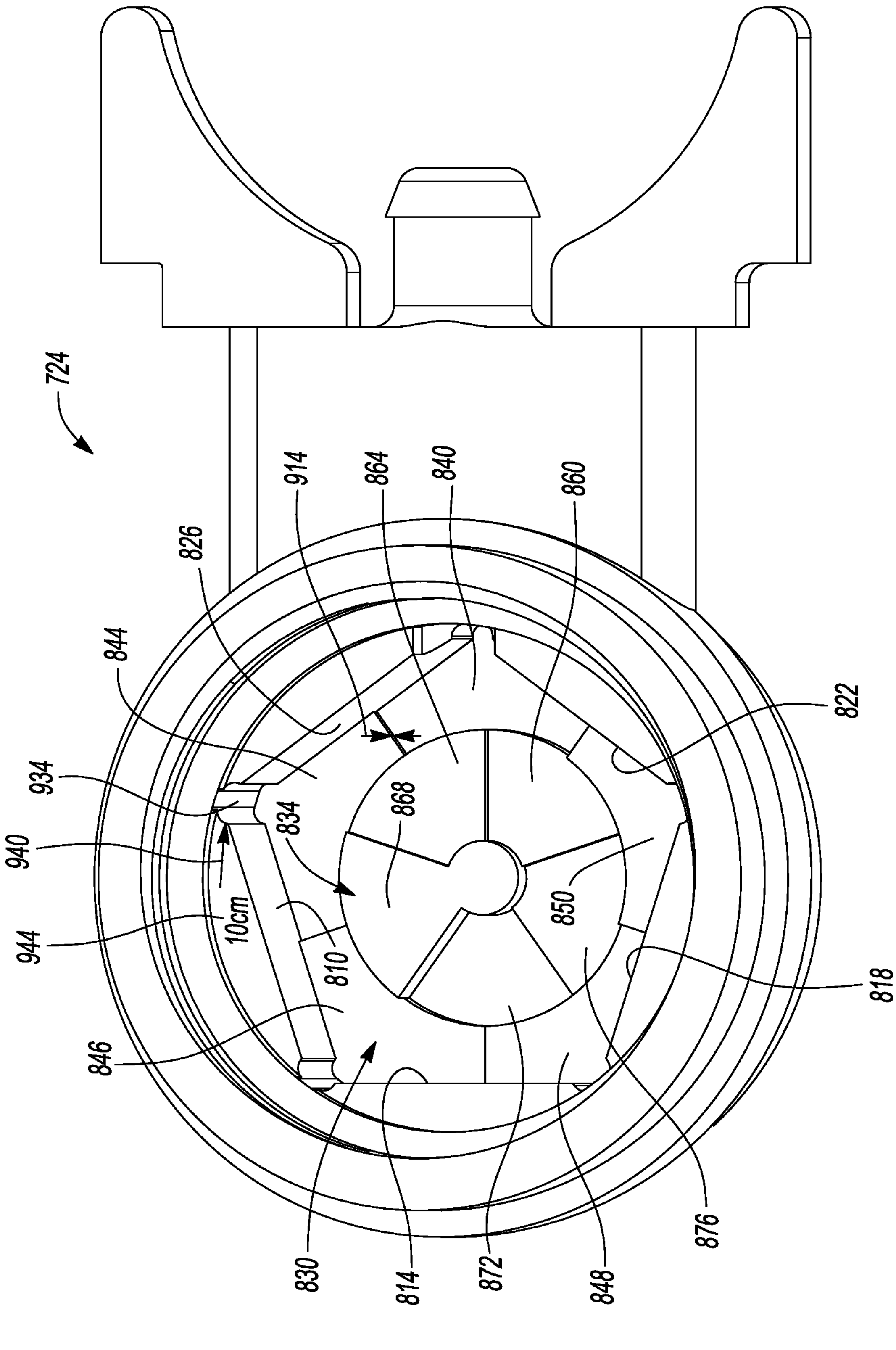
FIG. 12 is a detailed view of an interior of a cassette housing of the cassette assembly as illustrated in FIG. 11A, according to various embodiments.
Figure 13:
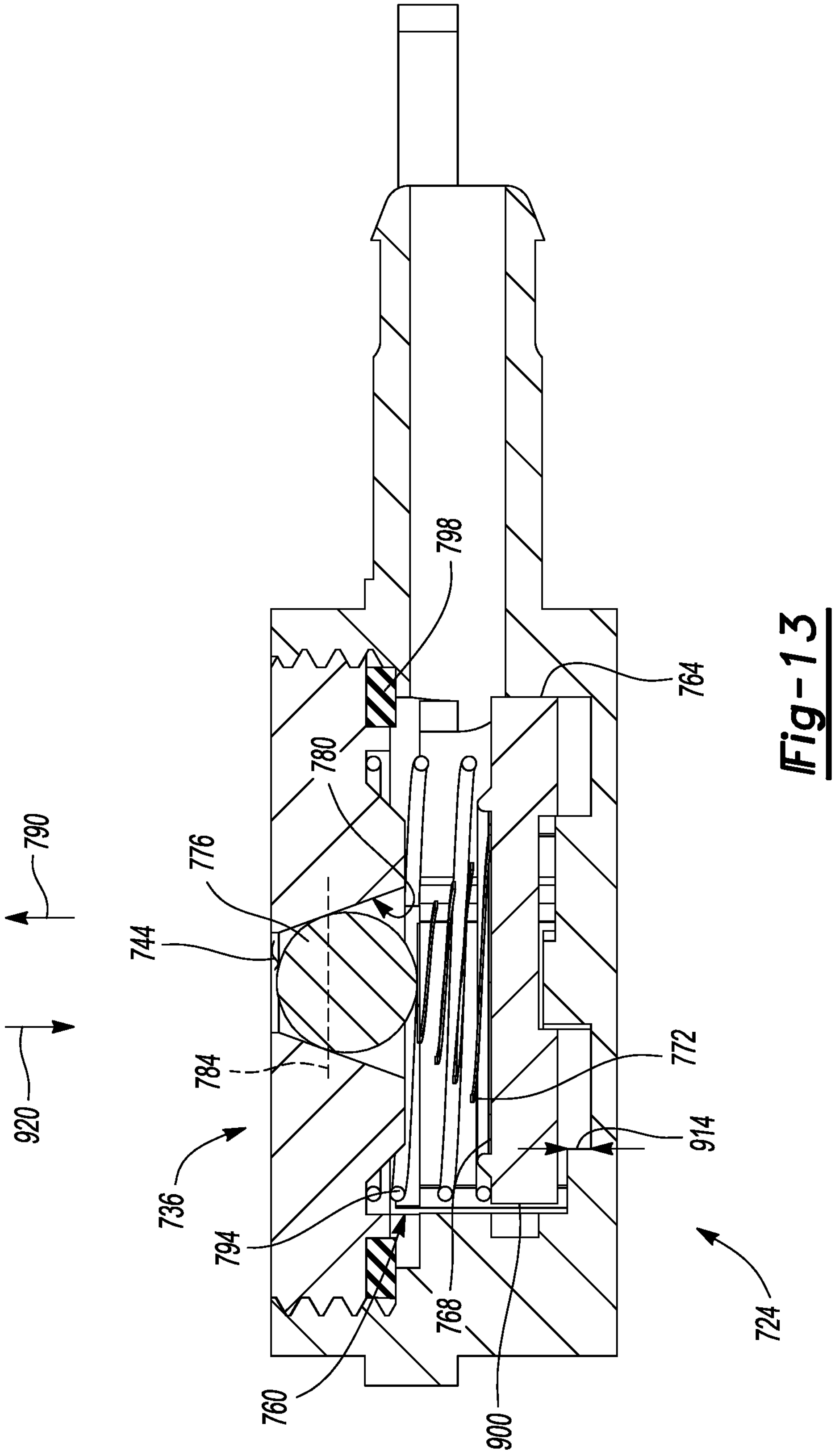
FIG. 13 is a cross-section view of an assembled cassette assembly taken along line 13-13 of FIG. 11A.
Figure 14A:
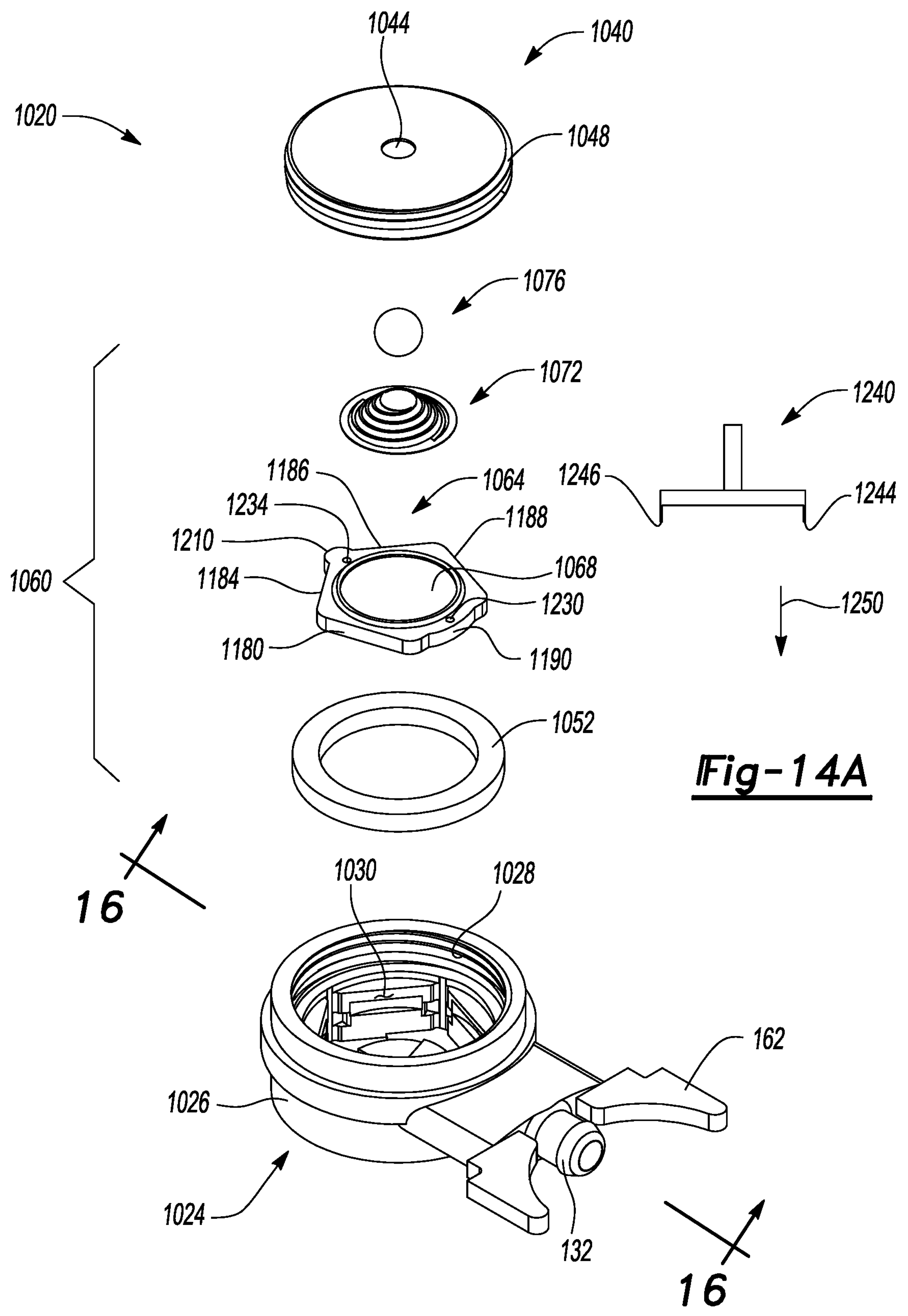
FIG. 14A is a first perspective exploded view of a cassette assembly, according to various embodiments.
Figure 14B:
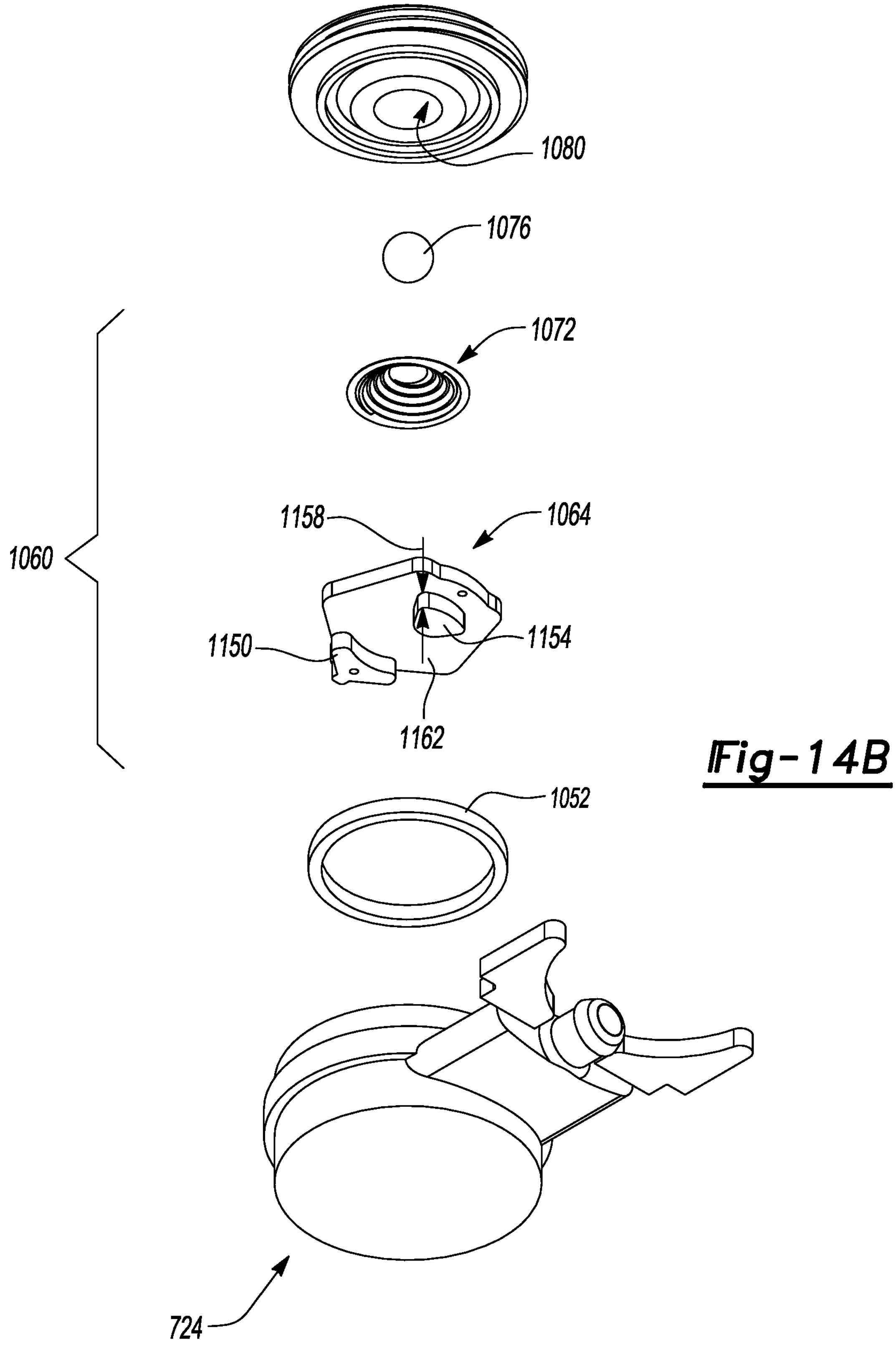
FIG. 14B is a second perspective view of an exploded cassette assembly of FIG. 14A.
Figure 15:
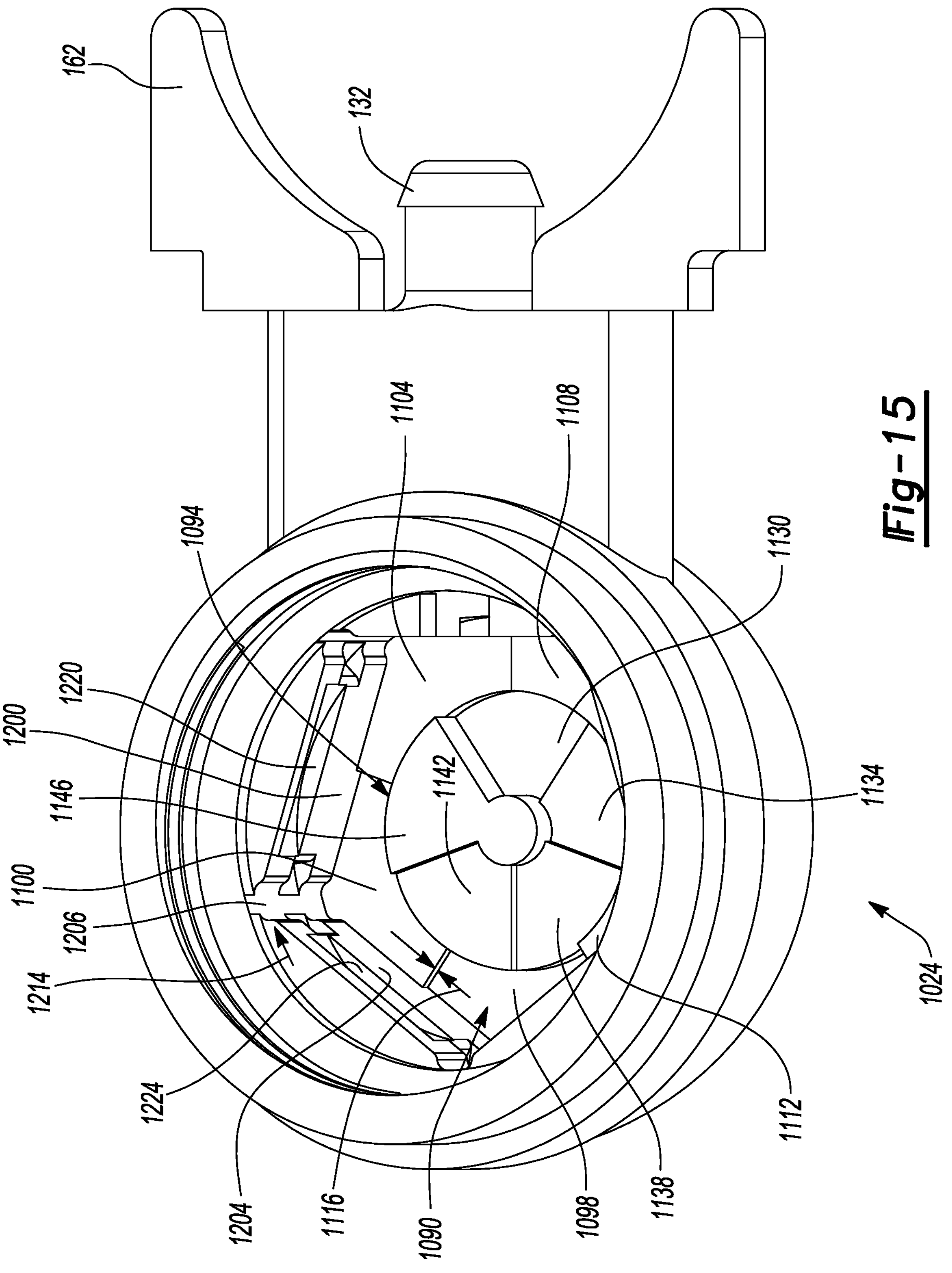
FIG. 15 is a detailed view of an interior of a cassette housing of the cassette assembly as illustrated in FIG. 14A, according to various embodiments.
Figure 16:
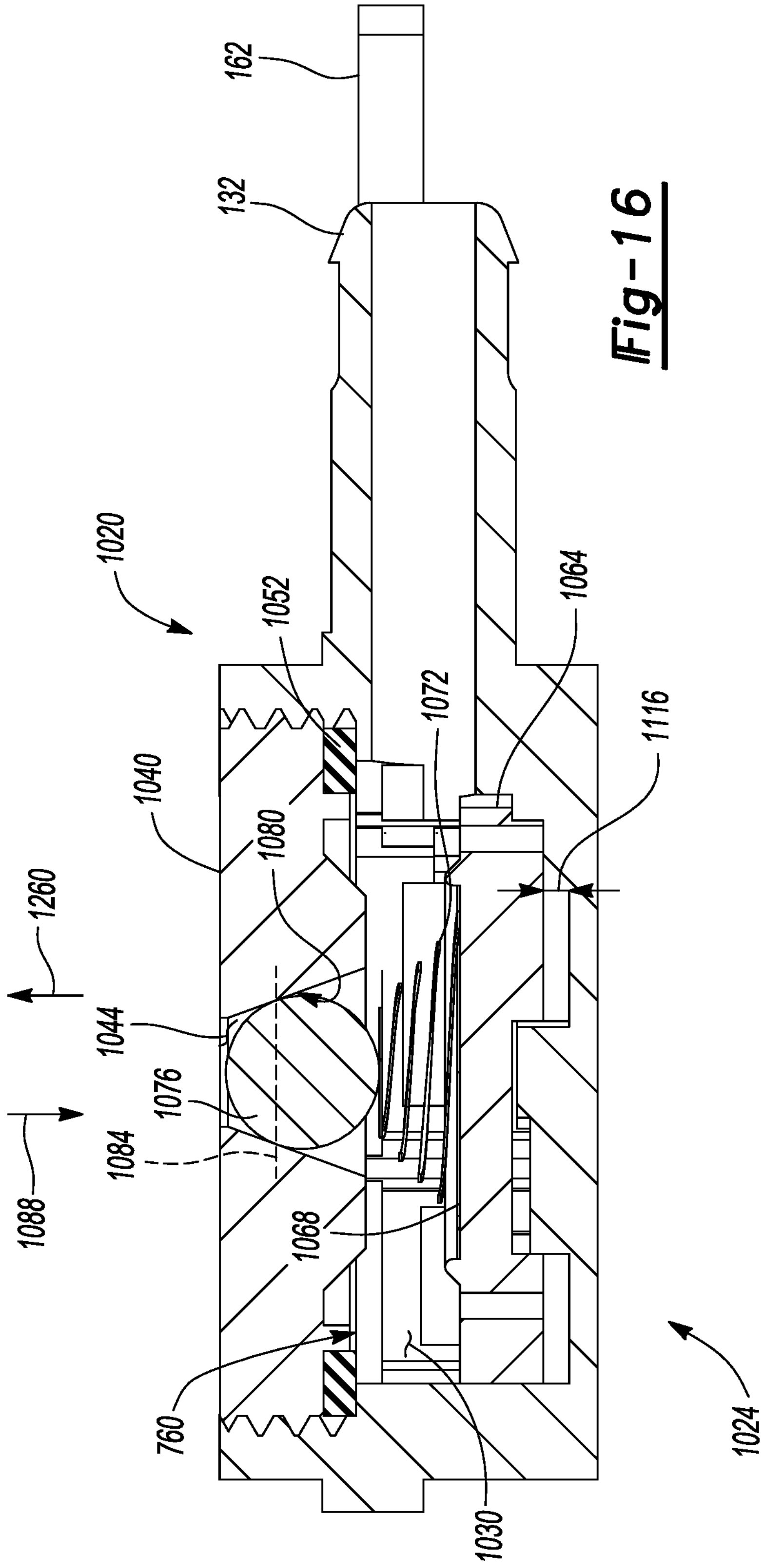
FIG. 16 is a cross-section view of an assembled cassette assembly taken along line 16-16 of FIG. 14A.

The cassette assembly 720 includes the rotor 764. As illustrated in FIGS. 11A and 11B, the rotor 764 may have a non-curved or circular outer edge. The rotor 764 may include an outer edge or geometry that may be a polygon that includes one or more facets, such as a plurality of substantially straight or planar edges 790. In various embodiments, the rotor 764 may include five edges, 790, 794, 798, 802, 806. Each of the edges 790-806 may engage an internal wall surface of the cassette housing 724. For example, as illustrated in FIG. 12, the cassette housing 724 may include a complementary number of walls 810, 814, 818, 822, 826. Accordingly, the cassette housing 734 may substantially define a pentagon depression or internal shape that may be complementary to an outer pentagon shape of the rotor 764. The complementary non-circular shapes may assist in holding the rotor 764 at a selected rotational position within the cassette housing 724.

As discussed above, the cassette housing may further include an open pressure selection portion, such as one or more selection areas. For example, the cassette housing 724 may include an outer selection area 830 and an inner selection area region 834. It is understood, however, that only a single one of the selection areas may be provided and two is merely exemplary. Similarly, as discussed above, the outer selection area 830 may include a selected number of portions that have differing heights that may vary the position of the rotor axially or relative to the seal position 784. In various embodiments, for example, five positions may be formed including a first position 840, a second position 844, a third position 846, a fourth position 848, and a fifth position 850. Similarly the inner selection region 834 may include five selection positions such as a first inner selection position 860, a second position 864, a third position 868, a fourth position 872, and a fifth position 876. Each of the respective positions of the outer selected region 830 and the inner selected region 834 may engage or contact a respective outer foot or projection 900 or an inner foot or projection 904. As discussed above, the projections 900, 904 may extend a selected distance from a bottom surface 910 that may be opposed or opposite the spring engaging surface 768.

Further, similar to the selection regions as discussed above, each of the individual steps of the respective outer selection regions 830 and the inner selection region 834 may differ in height relative to a base portion. For example, as illustrated in FIG. 12, the first portion 840 may be a base or floor of the cassette housing 724 and the first step 844 may include a selected height or distance 914 above or away from the surface 840 of the first portion 840. Each of the other portions or steps may include a selected distance from the previous or other selected steps and may, therefore, engage the respective projections 900, 904 at different or varying heights relative to the seal regions 784.

As discussed above, therefore, the rotor 764 may be rotationally positioned within the cassette housing 724 to vary the position of the spring engaging surface 768 relative to the bottom surface of the cassette housing 724 and the sealed position 784 of the seal region 780. As the rotor 764 is selectively positioned, the spring engaging surface 768 may be generally moved in the direction of the arrow 790 to decrease the spring distance of the regulating spring 772. As the spring distance is decreased (i.e., the spring is compressed) the biasing force applied to the seal ball 776 may be increased and, therefore, a greater pressure is required to open the valve mechanism 760 by the flow of material generally in the direction of arrow 920 into the inlet 744.

Further, the rotor 764 may include an indicator or a projection 930. The indicator or projection may be positioned in one or more recesses 934 or alignment depressions 934 that are formed between each of the wall surfaces 810, 814, 818, 822, 836. While the cassette housing 724 is understood to include a plurality of the recesses 934, only a single one is discussed here for clarity of the current discussion. The recesses may be provided to further rotationally fix the rotor 764 within the cassette housing 724. Accordingly, once the rotor 764 is selectively positioned within the rotor in a selected rotational position, the indicator 764 may be received within the recess 934 to assist in fixing the indicator 764 within the housing 724.

Further, markings may be provided within the cassette housing 724 to assist in identifying the result in opening pressure based upon the positioning of the rotor. For example, an indicator arrow or marking 940 may point or be directed to a selected one of the recesses 934. Further, a marking or indication 944 may be provided to provide a specific indication of an opening pressure that would be achieved or selected on the indicator 930 is positioned in the recess 934 indicated by the arrow 940. Accordingly, during assembly a user may understand the selected position or opening pressure when the rotor 764 is positioned within the cassette housing 724 in a selected position. The selected position may select or define a threshold or opening pressure of the valve mechanism 760, similar to that as discussed above.

Further, as discussed above, a final calibration may occur due to a rotation of the cap 736 within the cassette housing 724. As discussed above, the interaction of the internal threads 732 with the external threads 740 may allow for fine adjustments of the opening pressure between the steps due to a position of the rotor 764 within the cassette housing 724.

The rotor 764 may be held in a selected position axially, such as generally in the direction of the arrows 790, 920 with the return spring 794 or other appropriate mechanism. As discussed above, the rotor 764 may also be and/or alternatively be bonded or fixed within the cassette housing 724. In various embodiments, for example, a solvent may be applied to either the rotor 764 and/or the cassette housing 724 to bond the tube in a selected position. This solvent may then be evaporate and allow for a permanent bond of the rotor 764 within the cassette housing 724. Further, the positioning of the rotor 764 relative to the cassette housing 724 may be performed at a selected time, such as during a manufacturing, immediately prior or during an implantation procedure, or another appropriate time.

Turning reference to FIGS. 14A, 14B, 15, and 16, a cassette assembly 1020 is illustrated. The cassette assembly 1020 may include portions similar to that as discussed above, such as the cassette assembly 120. Accordingly, similar or identical portions will not be described in detail, however, variations or additional and/or alternative portions will be described in detail.

Generally the cassette assembly 1020 may include a cassette housing 1024 that includes an outer wall portion or body 1026. The outer wall portion 1026 may define an internal thread 1028 and also an internal volume 1030. The internal volume 1030 may include a volume of CSF, as discussed above. Further, the cassette housing may include the connection portion 162 and the outlet 132.

The cassette assembly 1020 may include a cap 1040 that defines an inlet 1044, similar to the inlet as discussed above. Accordingly the cassette housing 1024 may be filled with a selected material through the inlet 1044 through the cap 1040. Further the cap 1040 includes an external thread 1048 that may engage the internal thread 1028 of the cassette housing 1024. Therefore, the cap 1040 may be thoroughly engaged to the cassette housing 1024.

In various embodiments, the thread connection of the outer threads 1048 and the inner threads 1028 may form a seal to seal the volume 1030. In various embodiments the threaded engagement of the threads 1028, 1048 may form a convoluted or torturous seal. In various embodiments, however, for example including those discussed above and/or alternatively thereto, a seal member 1052 may be provided to assist in sealing or substantially closing the volume 1030 when the cap 1040 is placed on the cassette housing 1024. According to various embodiments, however, including those discussed above and further herein, the seal member 1052 may not be necessary or required given the interaction of the external threads 1048 with the internal threads 1028 and/or a sealing material positioned at the interaction of the threads.

The cassette assembly 1020 further includes a valve mechanism 1060. The valve mechanism 1060 may include an adjustment member that may also be referred to as a rotor 1064 that includes or defines a spring engaging or regulator engaging surface 1068. The spring engaging surface 1068 may engage or hold a biasing member, which may be a regulating spring 1072, relative to the cap 1040. The spring 1072 may engage or hold a sealing member 1076, such as a ball seal, relative to the cap 1040 that defines or forms a sealed region 1080. The seal region 1080 defines a seal position 1084, similar to that as discussed above. Accordingly, the pressure regulating spring 1072 may hold the sealing member or ball 1076 relative to the seal region 1080 with a biasing or a spring force until an inlet pressure, generally in the direction of arrow 1088, overcomes the force applied by the spring 1072 to allow inflow of fluid or material into the cassette housing 1024 such as within the volume 1030.

The amount of force required to move the sealing member 1076 out of the seal position 1084 (i.e., the threshold pressure) may be adjusted by altering the force applied by the regulating spring 1072 such as by selecting a compression of the spring 1072. The cassette housing 1024 may include or define an internal adjustment or selection area including one or more adjustment areas, similar to those discussed above. In various embodiments, the cassette housing 1024 may define an outer adjustment area 1090 and an inner adjustment area 1094. The outer adjustment area 1090 may include a selected number of steps or variable heights relative to a or from a first adjustment position 1098 through a selected number of other steps or positions, such as four other positions for a total of five positions, including 1100, 1104, 1108, and 1112. Similar to the adjustment areas discussed above, for example, a difference in height may be present from the first region 1098 to the second region 1100. The height difference may be a height or a distance 1116. The height 1116 may move the rotor surface 1068 closer to the seal region 1084 and decrease the height that the spring 1072 and, therefore, increase the spring force applied to the seal ball 1076. Accordingly, similar to the discussion above, positioning of the rotor further away or closer to the seal position 1084 may alter the force required to open the seal ball 1076 from the seal position 1084 and the seal 1080.

The adjustment region in the cassette assembly 1024 may also include the second adjustment region 1094. The second adjustment region may also include a selected number of adjustment positions, such as five adjustment positions 1130, 1134, 1138, 1142, and 1146. Each of these may again be positioned at different heights equivalent to the heights of the first adjustment position or portion 1090.

The adjustment positions 1090, 1094 may be engaged or contacted by one or more projections from the rotor 1064. The rotor 1064 may include a first projection 1150 which may be an outer projection and a second projection 1154 which may also be referred to as an inner projection. Each of the projections 1150, 1154 extend a distance 1158 from a surface 1162. The surface 1162 is generally opposed to the surface 1068 that contacts the spring 1072. Accordingly, as the projections 1150, 1154, or any appropriate number of projections, contacts one or more of the selected portions of the one or more adjustment regions 1090, 1094. The rotor 1064 may be moved closer to or further away from the seal position 1084 and, therefore, adjust or select a pressure applied by the regulating spring 1072 to the sealing member 1076. Nevertheless, due to the regulating spring 1072 the sealing member or ball 1076 may move out the seal 1080 to allow an inflow of fluid.

The rotor 1064 may be fixed within the cassette housing 1024 in a selected manner, including those discussed above such as with a retaining spring, bonding, or other appropriate connection. In various embodiments, either in addition to or alternative to the above-discussed holding systems, the rotor 1064 may be snap fitted to the cassette housing 1024.

The rotor 1064 may include a selected shape, such as a polygon shape including a selected number of sides, as exemplary illustrated including five sides 1180, 1184, 1186, 1188, and 1190. The rotor 1064, therefore, may be substantially pentagon in shape. It is understood, however, that the rotor 1064 may be formed in any appropriate shape such as any appropriate polygon shape including a selected number of sides. The rotor housing may include a complementary number of walls to engage or interact with the rotor 1064 to hold a rotor 1064 in a selected rotational position. In various embodiments, for example, a first wall 1200 and a second wall 1204 may engage two of the edges or walls of the rotor 1064. It is understood that the rotor housing 1024 may include any number of walls to engage the rotor 1064 and the discussion of the two walls 1200, 1204 is merely exemplary. In various embodiments, for example, five walls may be provided to interact with the five edges of the rotor 1064. Between the respective walls may be a recess or depression 1206 that may interact with an indicator 1210. The indicator may be engaged in the recess 1206, similar to the indicator 930, as discussed above. Further markings may be provided, such as an indication marking 1214 to provide an indication of a selected pressure or position of the rotor 1064 within the housing 1024.

One or more of the walls 1200, 1204 or any of the other walls may include one or more slots or ridges. For example, the wall 1200 may include a first slot 1220 and a second wall 1204 may include a second slot 1224. The edges, such as the edge 1184 may be received in the slot 1224 and the edge 1186 may be received in the slot 1220. Therefore, the indicator 1210 may be held within the recess 1206. Thus, the rotor 1064 may be snap fit into the cassette housing 1024.

In various embodiments, for example, the rotor 1064 may be formed of a material that may resiliently deform during insertion into the cassette housing 1024. Selected materials may include thermos-plastics like polypropylene, Acetal, polysulfone or polyethersulfone, combinations therefore and/or copolymers thereof. During insertion, the edges 1184, 11186 may deflect and then move into the slots 1220, 1224 when the rotor is moved into the housing 1020.

Further, additional tools or mechanisms may be used to assist in holding the rotor 1064 during insertion. For example, an assembly tool 1240 may contact or engage tool engaging holes or depressions, such as a first hole 1230 and a second hole 1234 of the rotor 1064. The tool 1240 may include a first tip 1244 and a second tip 1246 that engage the respective holes or depressions 1230, 1234 to allow for a press fit or force generally in the direction of arrow 1250 to press the rotor 1064 into the cassette housing 1024. The indicator 1210 may be aligned with one or more of the depressions, such as the depression 1206 and the tool 1240 may be engaged in the holes 1230, 1234 to press the rotor 1064 into the housing. The edges may resiliently deform and then snap or relax into the respective slots, such as the slot 1220 and the slot 1224. The rotor 1064 may thereafter be rotationally and axially held within the cassette housing 1024. Thus, the rotor 1064 engaging the selected adjustment regions 1090 and/or 1094 may define a position relative to the sealed position 1084 to generate a spring force or a biasing force against the seal member 1076.

Again, as discussed above, the rotor, according to various embodiments including the rotor 1064, may be fixed within the cassette housing 1024 to select a fixed and selected opening pressure that moves the seal ball 1076 generally in the direction of arrow 1088. Thus the rotor 1064 may be snap fit into the slots, as discussed above.

Further, the cap 1040 including the outer thread 1048 may be moved relative to the inner thread 1028 to adjust a force applied to the seal ball 1076. As discussed above, the threaded interaction may allow for a fine turning due to movement of the cap 1040 generally in the direction of arrow 1088 and/or the direction of arrow 1260. The movement of the cap 1040 relative to the rotor 1064 may fine tune or adjust to the pressure on the ball 1076 and the force applied by the regulating spring 1072 in adjustments finer than the adjustments of the adjustment regions 1090, 1094 due to the distances, such as the distance 1116.

Figure 17:
FIG. 17 is a schematic view of a spring having a selected free length and a second selected free length.

Turning reference to FIG. 17, as discussed above, a regulating biasing member 1280 may be provided in a valve mechanism, according to various embodiments, including the regulating spring or biasing member as discussed above. In various embodiments, as discussed above, a rotor or other mechanism may be used to adjust an amount of compression, such as through a height or spring force applied by the biasing member relative to a seal or seal position. According to various embodiments, in addition to the rotor and/or alternatively thereto, the biasing member 1280 may have its length adjusted. For example, as illustrated in FIG. 17, the biasing member 1280 may include a first height 1284 and/or a second height 1288. The second height 1288 be greater than the first height 1284 of the biasing member 1280. Due to the greater height or free length of the biasing member 1280 the force applied by the biasing member 1280 relative to a sealing position relative to any fixed base position or distance from the sealing position may be increased. Accordingly, the opening or cracking force of the seal mechanism may be increased by only increasing the free length or height, such as the length 1288 relative to the first length 1284.

In various embodiments, a single spring or biasing member may be provided for installation into a plurality of different valve mechanisms, such as the valve mechanism 60. An opening or cracking force may be selected or achieved by lengthening or stretching the biasing member 1280, such as a regulator spring, to one of a plurality of selected links. In various embodiments, for example, the first length 1284 may include a first or provide a first opening pressure of a valve mechanism. Whereas stretching the biasing member to the second length 1288 may include a different or achieve a different or second opening pressure. Accordingly, in various embodiments, the opening pressure or opening force required to open the valve mechanism may be adjusted or achieved by selecting or forming the spring or biasing member 1280 a selected length. Achieving the selected length may include stretching or compressing the spring after the spring is formed.

While adjusting the biasing or spring member 1280 may be provided in addition to and/or alternatively to the use of a rotor to achieve a selected force on the sealing member, as discussed above. In various embodiments, however, the use of adjustment of the spring member 1280 may alone and/or substantially alone be used to adjust or select an opening force applied or required to open a valve member.

Figure 18A:
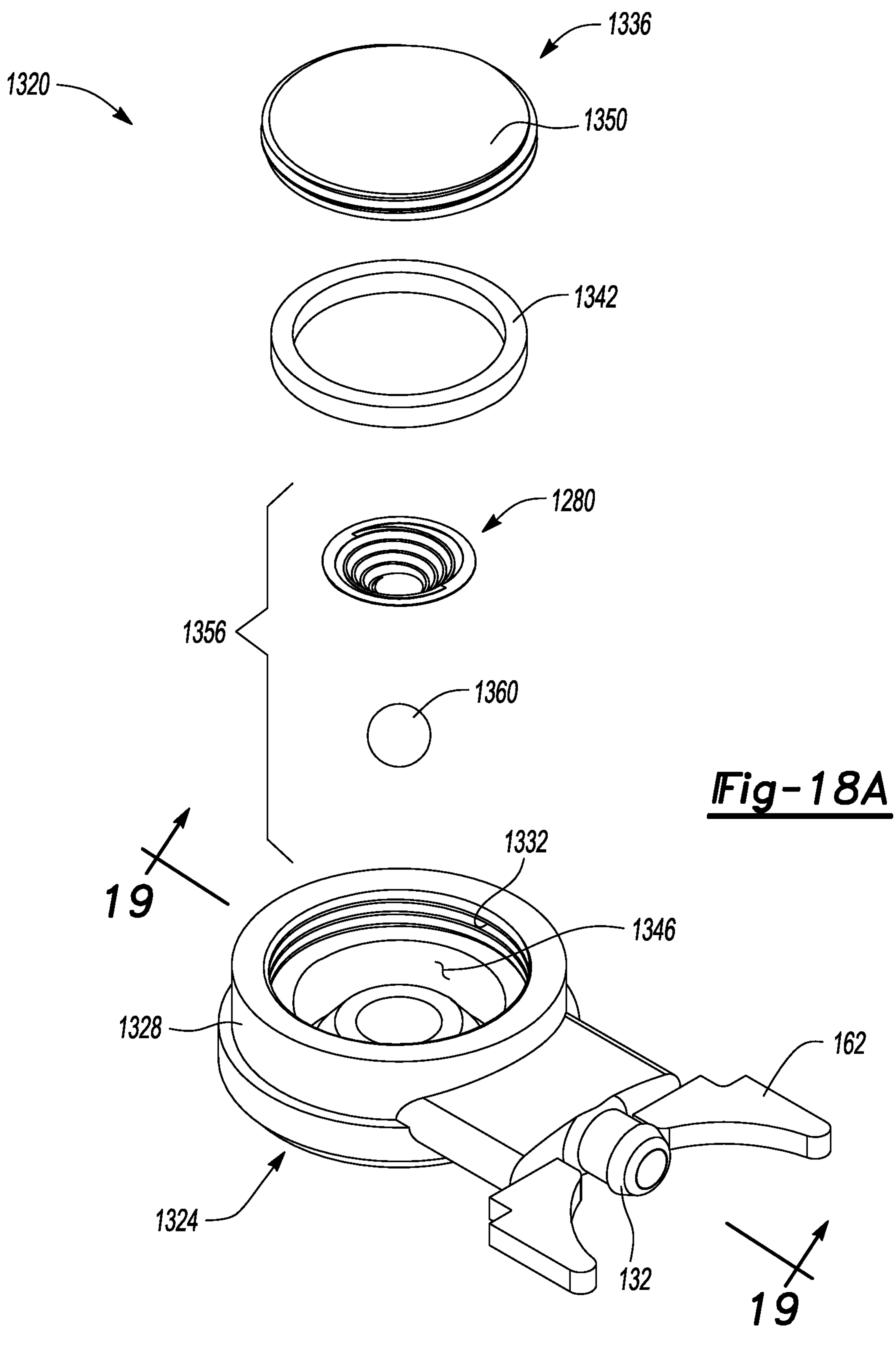
FIG. 18A is a first perspective exploded view of a cassette assembly, according to various embodiments.
Figure 18B:
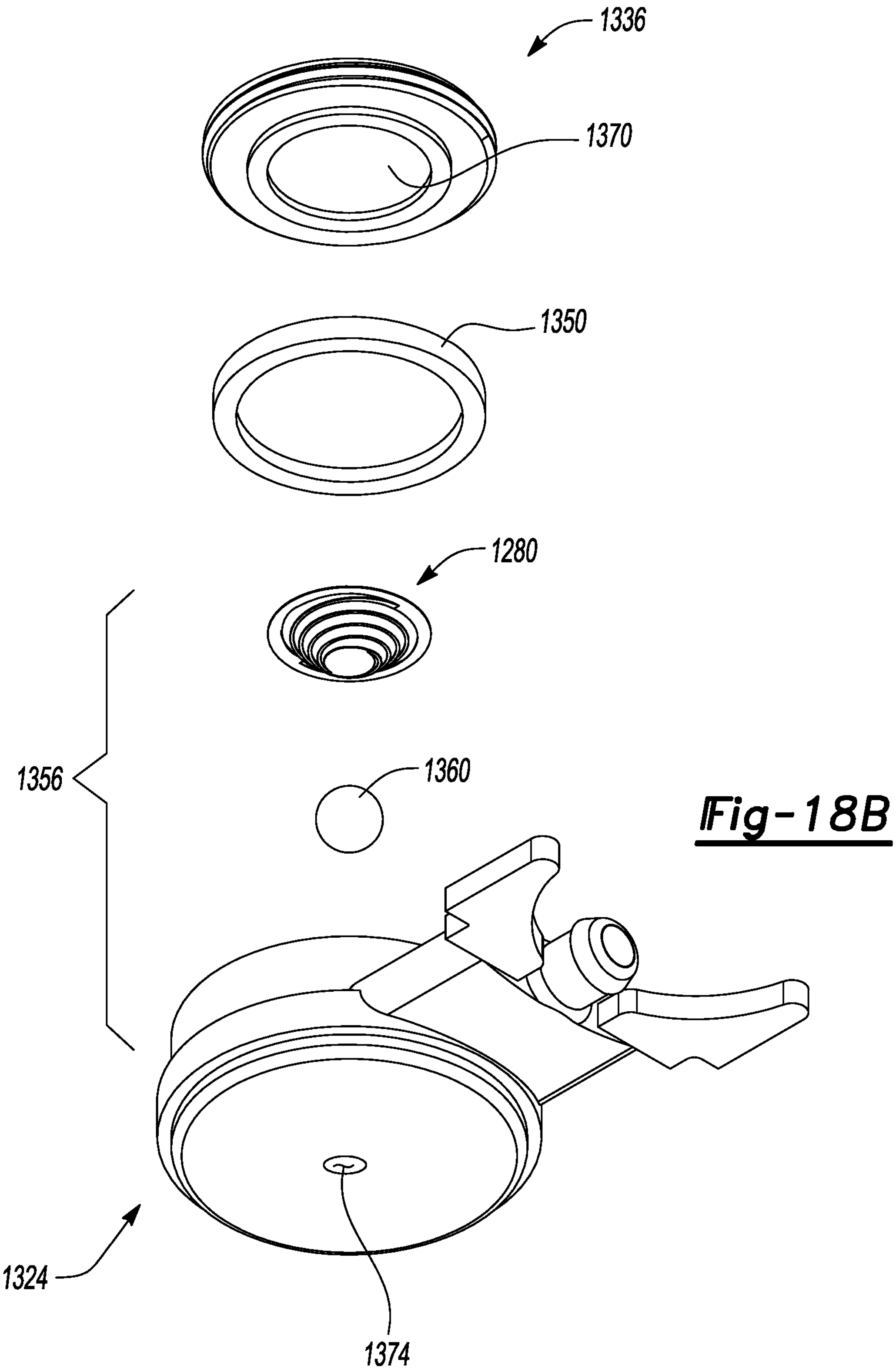
FIG. 18B is a bottom perspective view of an exploded cassette assembly.
Figure 19:
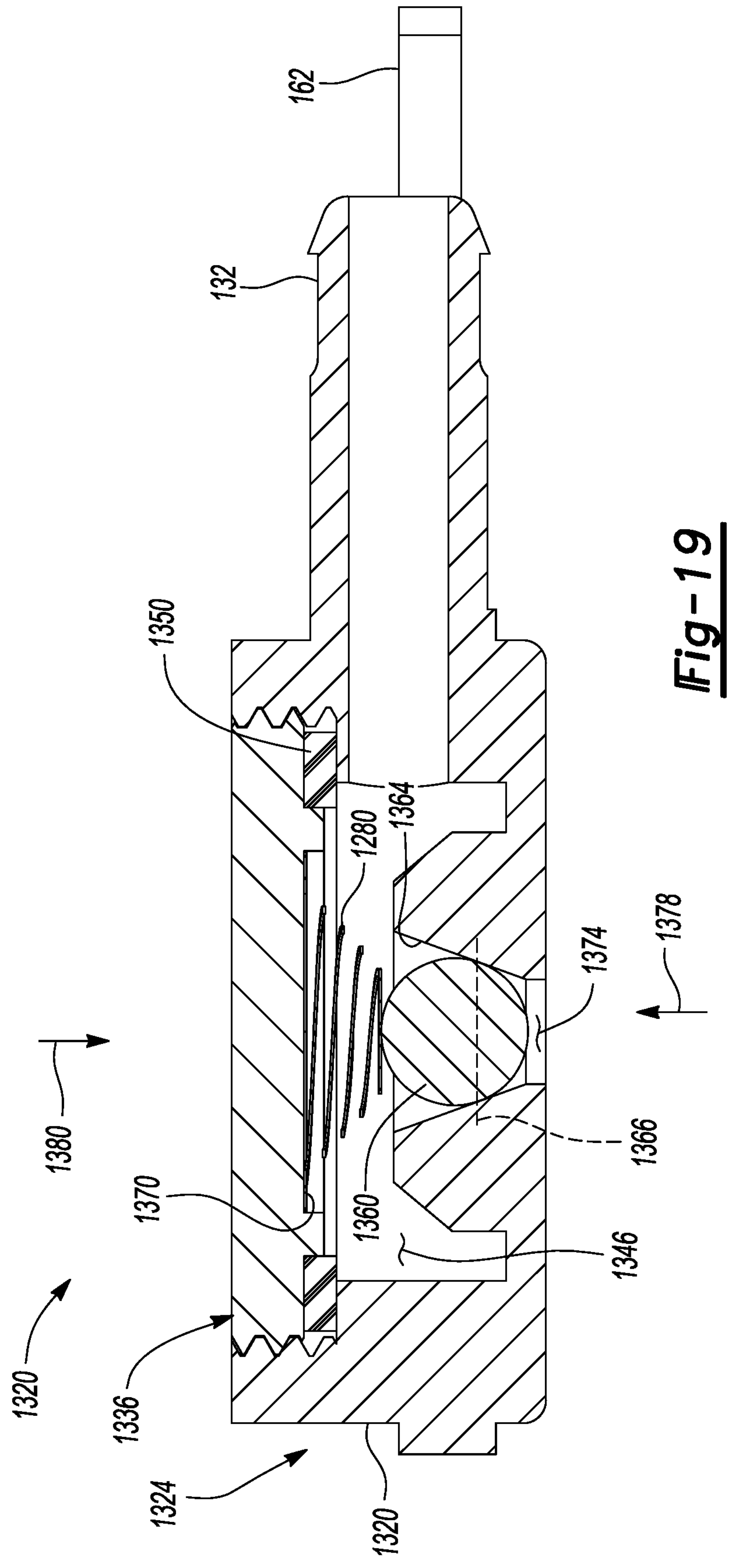
FIG. 19 is a cross-sectional view of the assembled cassette assembly taken along line 19-19 of FIG. 18A.

According to various embodiments, with continuing reference to FIG. 17 and additional reference to FIGS. 18A, 18B, and 19, a cassette assembly 1320 is illustrated. The cassette assembly 1320 may include portions similar to those discussed above, such as in the cassette assembly 120. The cassette assembly 1320, therefore, may include a cassette housing 1324 that includes an outer wall 1328 the outer wall 1328 may define or form an internal thread 1332. Further, a cap 1336 may include or form an outer or external thread 1342. The external thread 1342 may threadably engage the internal thread 1332. The interaction of the cap 1336 with the housing 1324 may form or define a cassette volume 1346. Further, as discussed above, the threaded interconnection of the external threads 1342 in the internal threads 1332 may form a seal to seal or define the volume 1346. In various embodiments, however, an additional seal member, such as an O-ring or seal 1350 may be provided between the cap 1336 and the cassette housing 1324 to assistant sealing the cap 1336 to the housing 1324.

Further, the cassette assembly 1320 may include or define a seal mechanism 1356. The seal mechanism 356 may include or be defined by or formed by the regulating spring 1280. As discussed above, the regulating spring 1280 may be stretched or provided at a selected height, such as the height 1284 and/or the height 1288. The sealing mechanism 1356 may further include a sealing member, such as a sealing ball 1360. The sealing ball 1360 may engage a seal 1364 that may be a conical or truncated conical portion. The seal 1364 may be a truncated cone. Further, the seal member 1360 may have a seal position 1366 similar to that discussed above. Accordingly, the height of the biasing member 1280 may be stretched to select a force applied to the sealing member 1360 between a spring contacting surface 1370 of the cap 1336 and the seal position 1366.

As illustrated in FIGS. 18A to 19, the biasing member 1280 may directly contact the cap 1336, such as at the surface 1370. Accordingly, the opening force of moving the sealing member 1360 from the sealed position 1366 may be provided by the height of the biasing member 1280 when contacting the cap 1336. The cassette housing 1324, according to various embodiments (including those discussed above), may define an inlet 1374 that allows for inlet of a fluid generally in the direction of arrow 1378. The biasing member 1280 may hold the sealing member 1360 against the seal 1364 until a force overcomes the biasing force of the spring member 1280. Nevertheless, as discussed above, the cassette assembly 1320 need not include an additional rotor or adjustment mechanism. According to various embodiments, the rotor may be used in addition to and/or alternatively to selecting a height of the biasing or spring member 1280, according to various embodiments.

Further the threaded engagement of the external threads 1342 and the internal threads 1332 may also operate to move the surface 1370 generally in the direction of arrow 1378 away from the sealing position 1366 or in the direction of arrow 1380 toward the sealing position 1366. Thus, by threading or unthreading the cap 1336, a further adjustment, as discussed above, to the force applied to the sealing member 1360 may be made.

Further, as illustrated in FIGS. 18A to 19, the inlet 1374 may be formed through the cassette housing 1324 rather than the cap 1336. The seal 1364 may also be formed at the cassette housing 1324 rather than at the cap 1336. Thus, according to various embodiments, the inlet may be positioned relative to the seal member 1360, according to various embodiments, in any appropriate position.

The biasing member 1280 may further be fixed to the cap 1336 at the surface 1370 in an appropriate manner. For example, the biasing member 1280 may be adhered to the cap 1336, such as with an adhesive or other bonding material or system. In various embodiments, for example, the biasing member 1280 may be bonded to the cap 1336 by providing a solvent that dissolves a selected portion of the cap 1336 and the spring 1280 is there by bonded to the cap 1336.

Figure 20A:
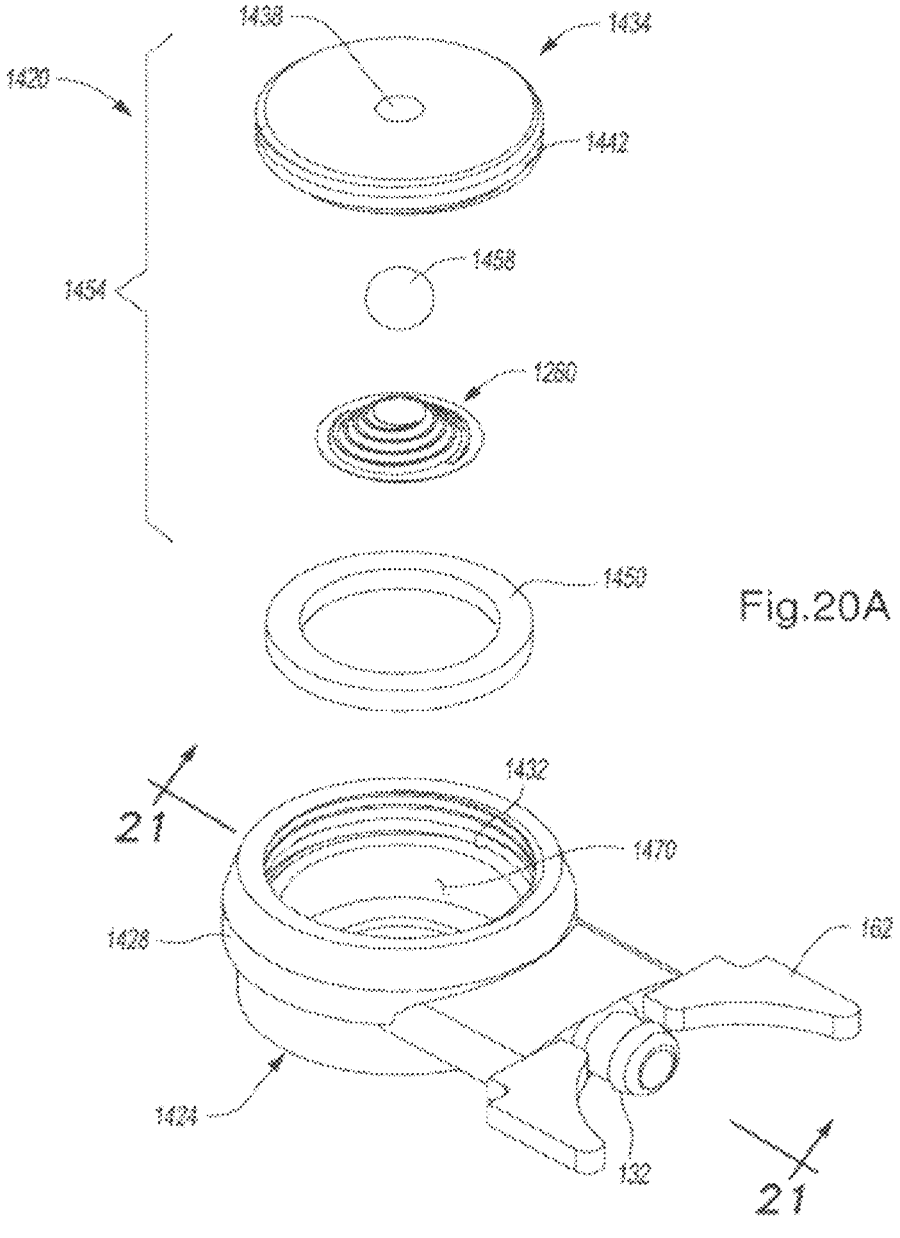
FIG. 20A is a top perspective view of an exploded cassette assembly, according to various embodiments.
Figure 20B:
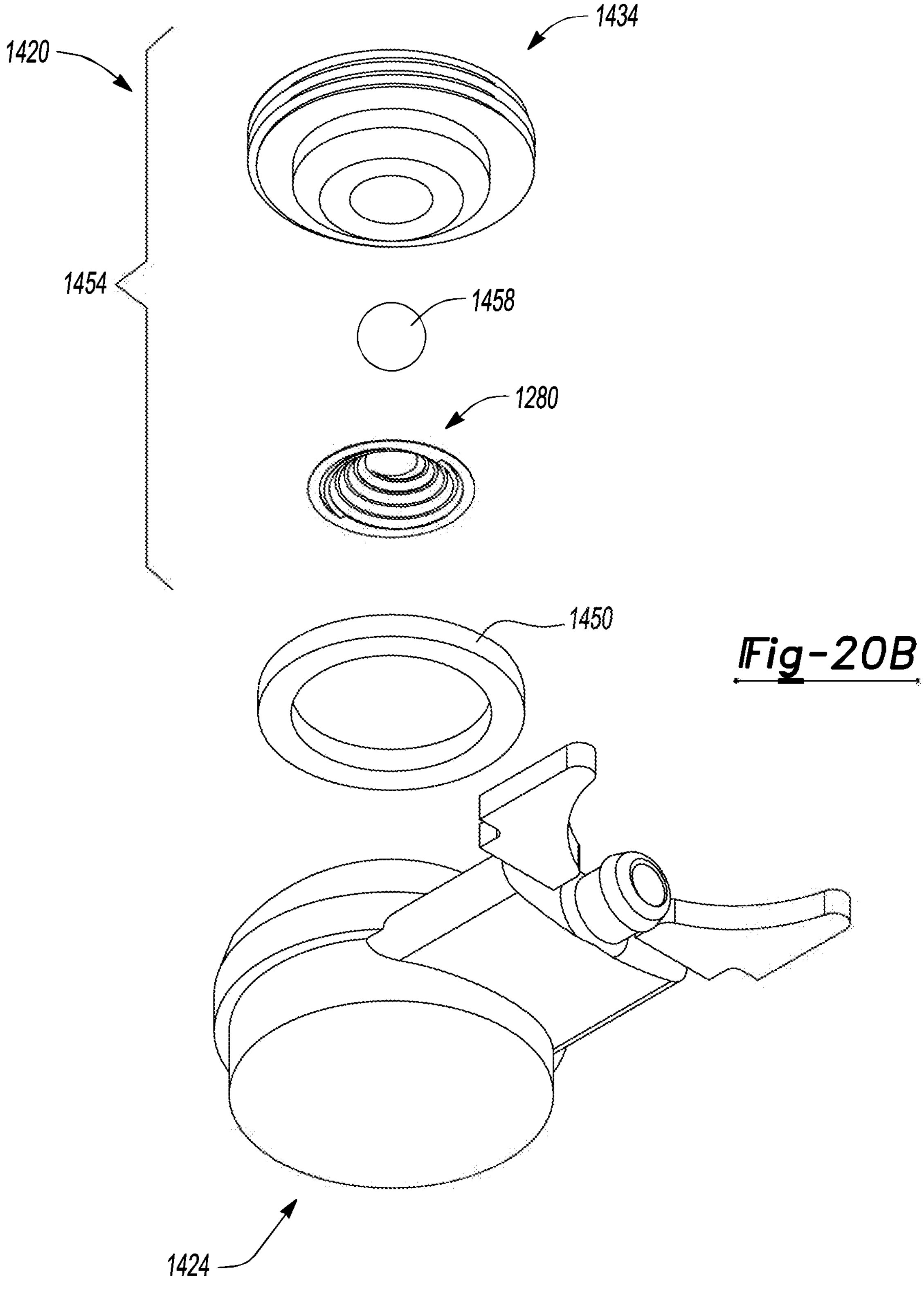
FIG. 20B is a bottom perspective view of an exploded cassette assembly, according to various embodiments.
Figure 21:
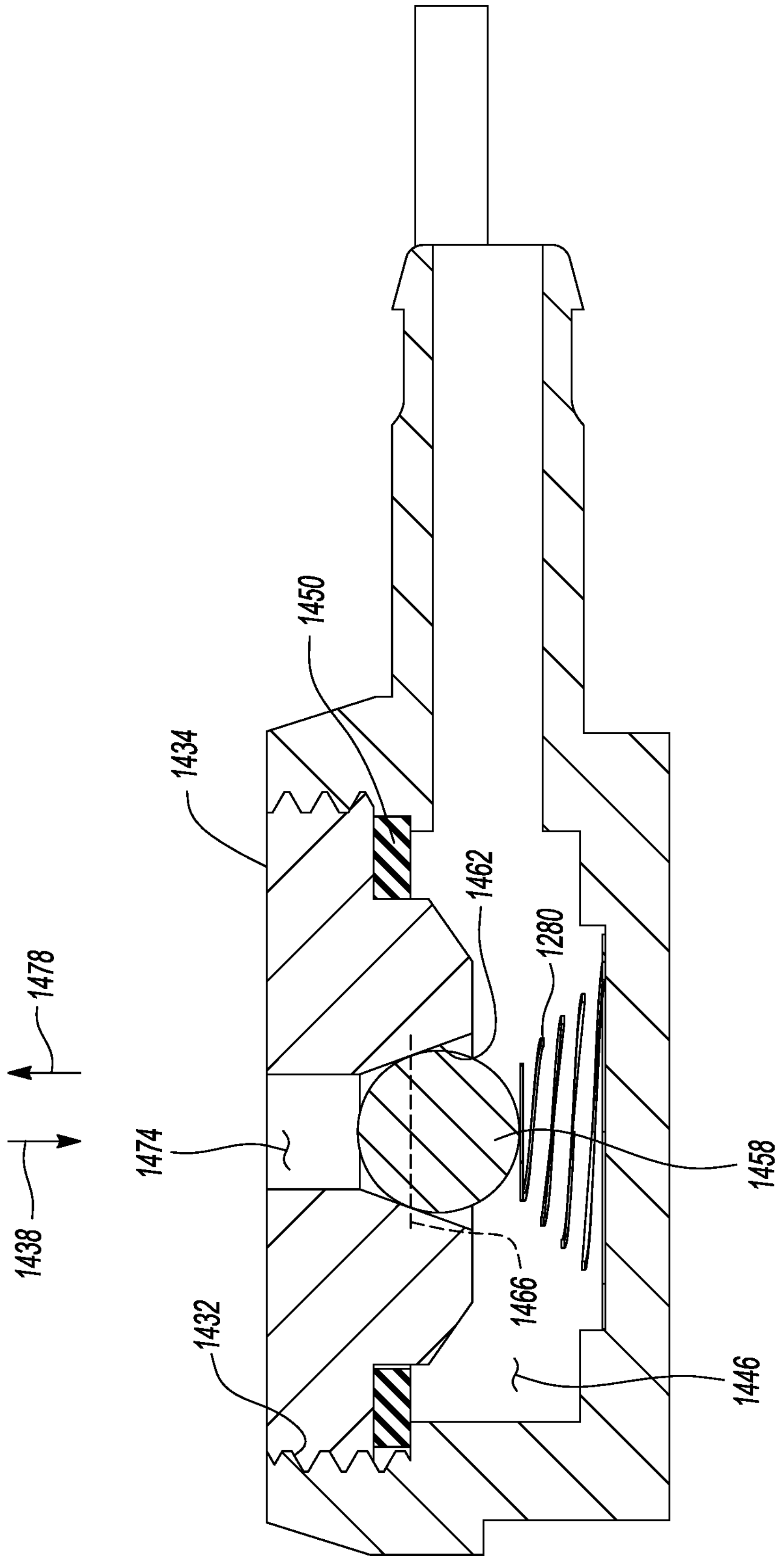
FIG. 21 is a cross-sectional view of the assembled cassette assembly taken along lines 21-21 of FIG. 20A.

With continuing reference to FIG. 17 and additional reference to FIGS. 20A, 20B, and 21, a cassette assembly 1420 is illustrated. The cassette assembly 1420 may include portions similar or identical to those discussed above, and those portions will not be discussed in greater detail here. Accordingly, the cassette assembly 1420 may be included in the valve assembly 60, in addition to and/or alternatively to the cassette assemblies as discussed above. The cassette assembly 1420 may include a cassette assembly housing 1424 that includes an outer wall 1428 that defines an internal thread 1432. Further, the cassette housing 1424 may include the connection 132 and the connection 162. The cassette assembly 1420 may include a cap or top 1434 that defines or forms an inlet 1438. The cap 1430 may define an external thread 1442. The external thread 1442 may threadably engage the internal thread 1332 of the cassette assembly housing 1424.

The interaction of the cap 1434 with the cassette assembly housing 1424 may form or define a volume 1446. As discussed above, according to various embodiments, the thread interaction of the threads of 1432, 1442 may seal the volume 1446 at least through the cap edges 1434. In various embodiments, however, an additional sealing member 1450 may also be provided between the cap 1434 and the housing 1424. Thus, the flow of fluid through the cassette assembly 1420 may be through the inlet 1438 and the outlet 132.

Further, the cassette assembly 1420 may include a valve mechanism 1454. The valve mechanism 1454 may include the biasing member 1280, as discussed above. The biasing member 1280 may form a biasing force against a sealing member 1458 by selecting or forming a length or free length of the biasing member 1280.

The valve mechanism 1454 includes the sealing member 1458 which may be held or engaged in a seal 1462. The sealing member 1458 may be sealed at a seal position 1466 within the seal 1462. The length or height of the biasing member 1280 may achieve or form the sealing force are closing force of the seal member 1458 into the seal 1462. The seal 1462 may, as discussed above, be formed as a cone or truncated cone, such that the sealing member 1458 may be pressed into the seal 1462 with the regulating or biasing member 1280.

Is illustrated in FIGS. 20A to 21, the biasing member 1280 may be fixed or held it to a spring engaging surface 1470 within the housing 1424. Accordingly, as discussed above, the biasing member 1280 may alone or substantially alone be used to achieve a selected cracking or opening force of the sealing member 1458 from the seal 1462. As discussed above, a rotor may be used to adjust the position of the biasing member 1280 relative to the seal position 1466, however, such a router is not required according to various embodiments.

The biasing member 1280 may be bonded to the engaging surface 1470 in an appropriate manner, including those as discussed above. The biasing member 1280 may be adjusted to a selected free height, such as the height 1284 and/or the high 1288 to achieve a selected opening force to allow flow of a material through the inlet 1438 generally the direction of arrow 1474. Thus, the cassette assembly 1420 need not include a rotor, but may alternatively include one as discussed above. The opening force may be further adjusted or tuned by the threaded engagement of the cap 1434 with the cassette housing 1424. As discussed above movement of the cap 1434 by the threaded engagement or interaction may move the cap 1434 generally in the direction of arrow 1474 and/or in the direction of the arrow 1478 to adjust or select a pressure applied to the sealing member 1458 in the cassette assembly 1420.

Accordingly, the cassette assembly, according to various embodiments, may be provided in the valve assembly 60 as discussed above. Further, various cassette assemblies may include various features that may be interchanged or used alternatively with one another, as also discussed above. The rotor may or may not be provided to achieve a selected opening pressure, as long as the opening pressure may be selected such as by adjusting the length of the spring alone or biasing member alone. The rotor, however, may be provided to allow for selection, such as efficient selection, or a particular opening pressure. The particular selection may allow for similar or multiple pieces to be used to form vale assemblies of several selected and/or different opening pressures. Other mechanisms, such as the threaded cap adjustment and/or the free length of the spring adjustment may allow for fine tuning and/or finer opening pressure selections or adjustments.

The number of projections of the rotor to interact with a selection region, as discussed above, may be provided in an appropriate manner to select or maintain a selected height or position of the rotor within the various cassette housings. In addition, the rotor may be provided in an appropriate geometry to interact with the cassette housing to achieve a rotational and/or axial position to maintain the selected position of the rotor to maintain a selected pressure or height of the biasing member, also referred to as a regulating spring or member, within the cassette assembly.

In various embodiments, as discussed above, the valve assembly 60 may include the inlet 80 and the outlet 84. The inlet 80 and the outlet 84 may be generally aligned and/or coaxial along an axis A (FIG. 2). In various embodiments, the cassette assembly, such as the cassette assembly 120 may include the valve mechanism or cassette inlet 124 generally along or having a central axis B and the outlet 132 may extend along an axis C. The axis B may not be aligned with the axis C. In various embodiments, as illustrated above, axis B may be substantially orthogonal to axis C. Thus, at least one of the inlet or the outlet of the cassette assembly, according to various embodiments, may not be aligned with the axis A.

As discussed above the valve assembly 60 may be provided in the shunt assembly 10 to assist in providing a selected flow rate and/or pressure within the ventricle of the subject. In various embodiments, the valve assembly 60 may include the cassette, according to various embodiments as discussed above such as the cassette 120. In various embodiments, however, the valve assembly 60 may include additional and/or alternative cassette assemblies. For example, as illustrated in FIGS. 22, 23, 24, 25, and 26 a valve assembly 1560 is illustrated. The valve assembly 1516 may include various portions that are similar or identical to those discussed above which will be discussed only briefly here. Briefly, and with returning reference to FIGS. 1-4, the valve assembly 1560 may include an inlet 1564, a passage 1568, a reservoir 1572 a flow-limiting chamber assembly 1576 including a chamber cover 1580 and a chamber flow control 1584 and an outlet 1588. The valve assembly 1560 may further be positioned on a sheet or cover 1592. Accordingly, the valve assembly 1560 may include various portions that are similar to those discussed above, such as in the valve assembly 60.

Figure 24:
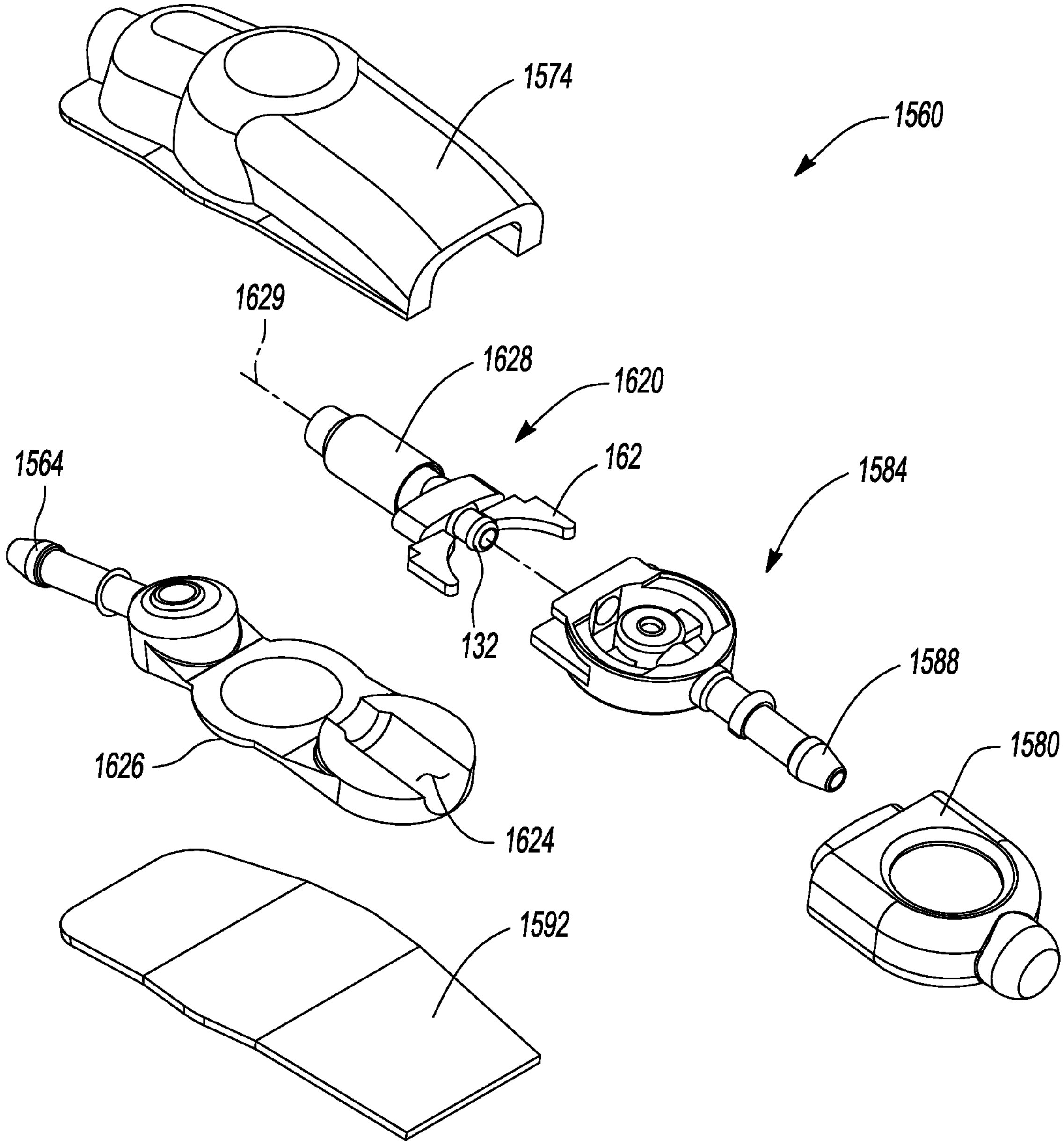
FIG. 24 is an exploded view of the valve assembly of FIG. 22.

The valve assembly 1560, however, may include a cassette assembly 1620 positioned within the cover or dome 1574. The cassette assembly 1620 may be similar in various features to the cassette assemblies as discussed above, such as the cassette assembly 120. The cassette assembly 1620 may, however, generally be elongated as illustrated in FIG. 24. The cassette assembly 1620 may include the outlet 132 in the connection portions 162 to interconnect with the flow limiting portion 1584 within the cover 1580. Further the cassette assembly 1620 may be held within a cassette receiving portion 1624 of a base 1626 of the valve assembly 1560. The cassette receiving section 1624 may be formed to receive a portion of the cassette assembly 1620, such as an inlet or first side or portion 1628.

Figure 22:
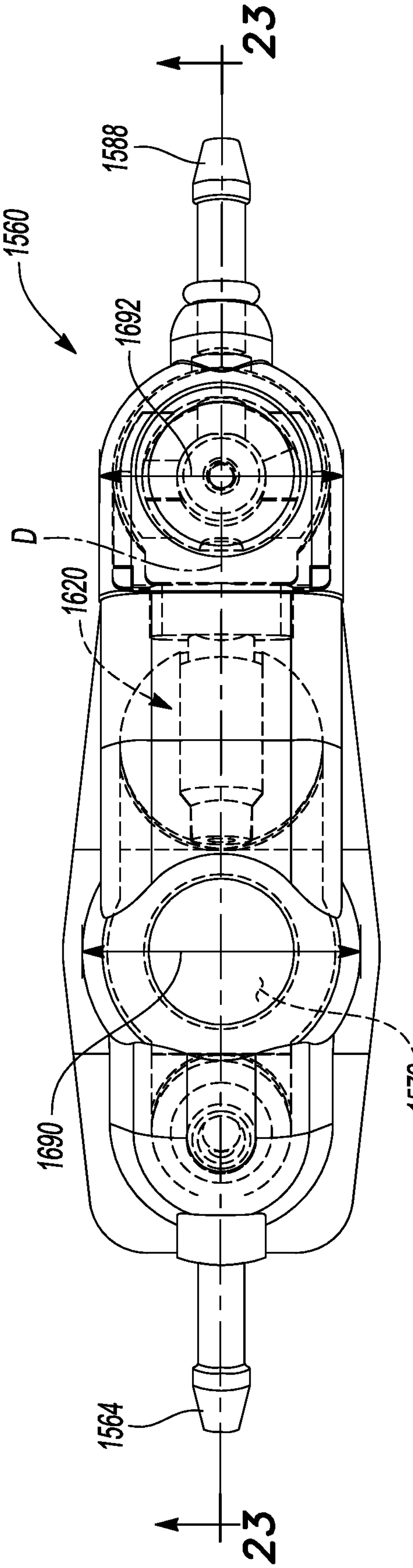
FIG. 22 is a top perspective view of a valve assembly, according to various embodiments.
Figure 23:
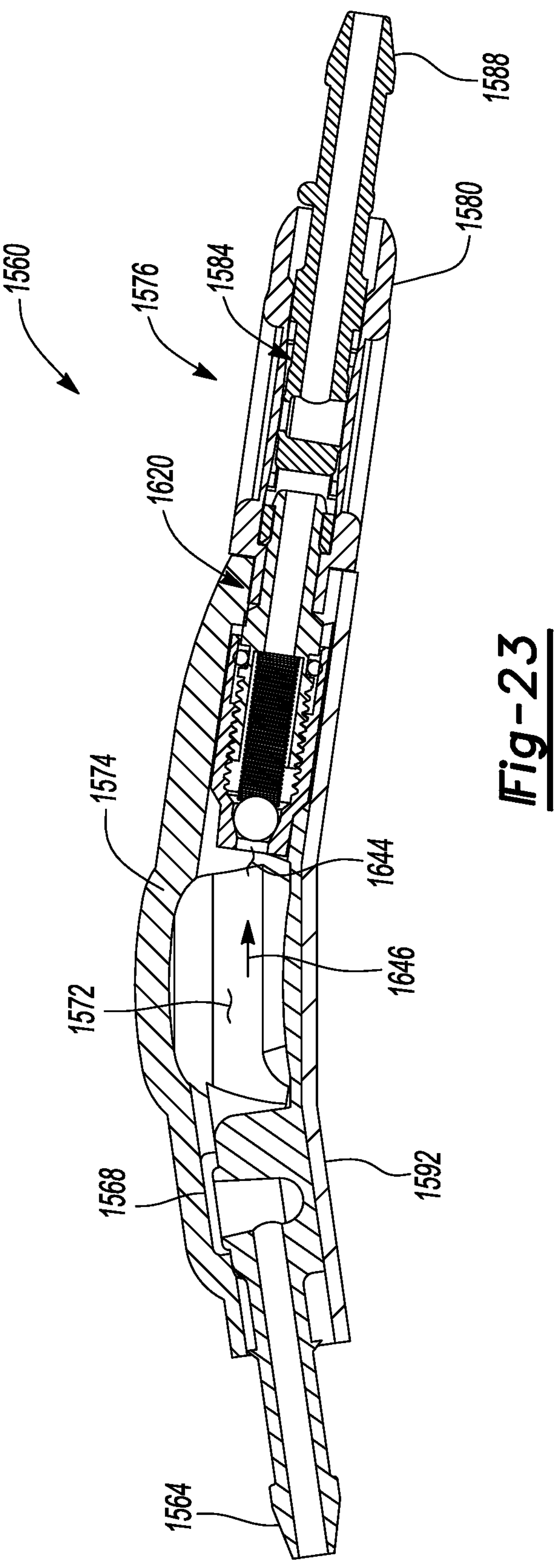
FIG. 23 is a cross-sectional view of the valve assembly of FIG. 22 taken along line 23-23.
Figure 25:
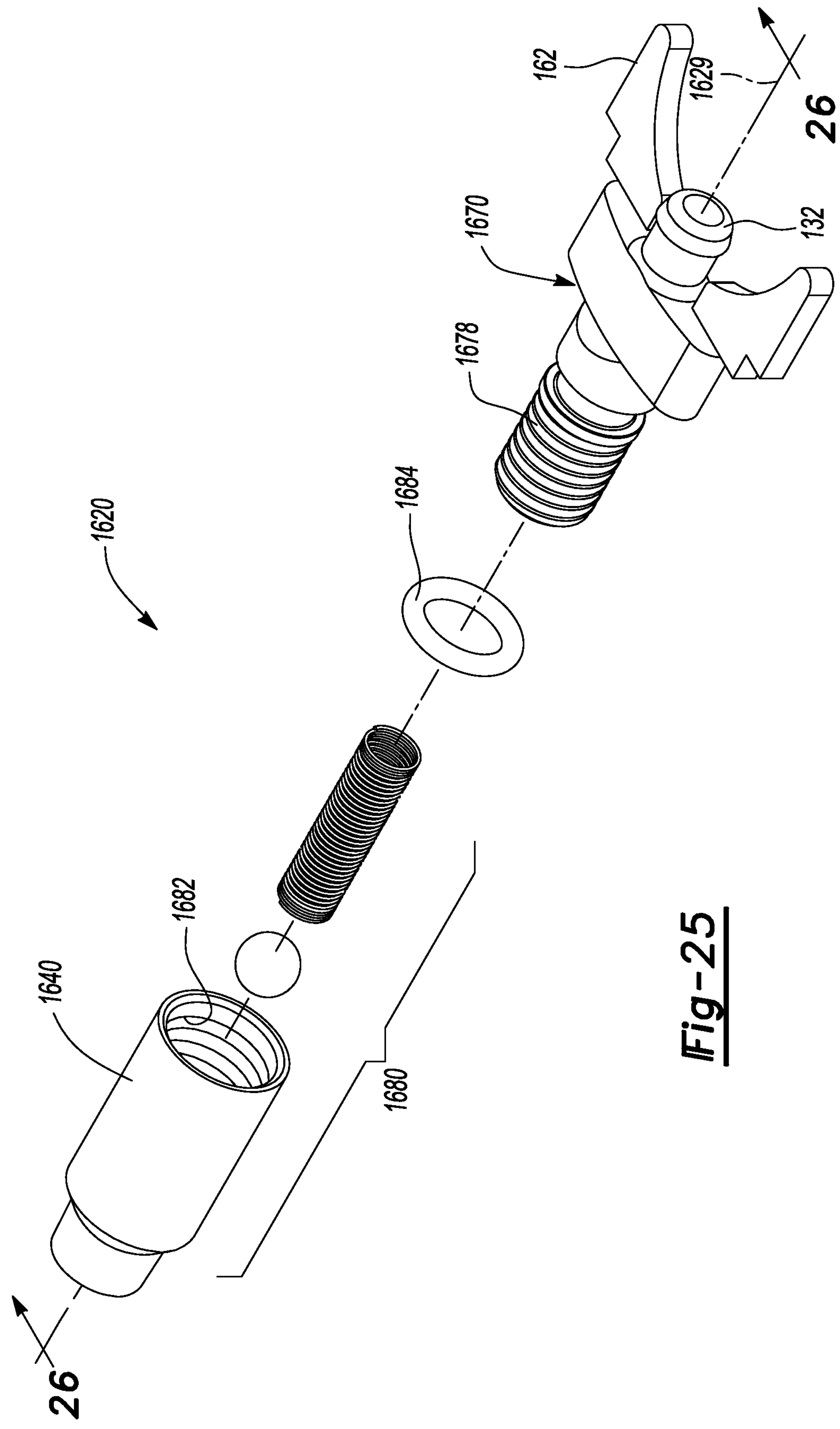
FIG. 25 is an exploded perspective view of a cassette assembly of the valve assembly of FIG. 24.
Figure 26:
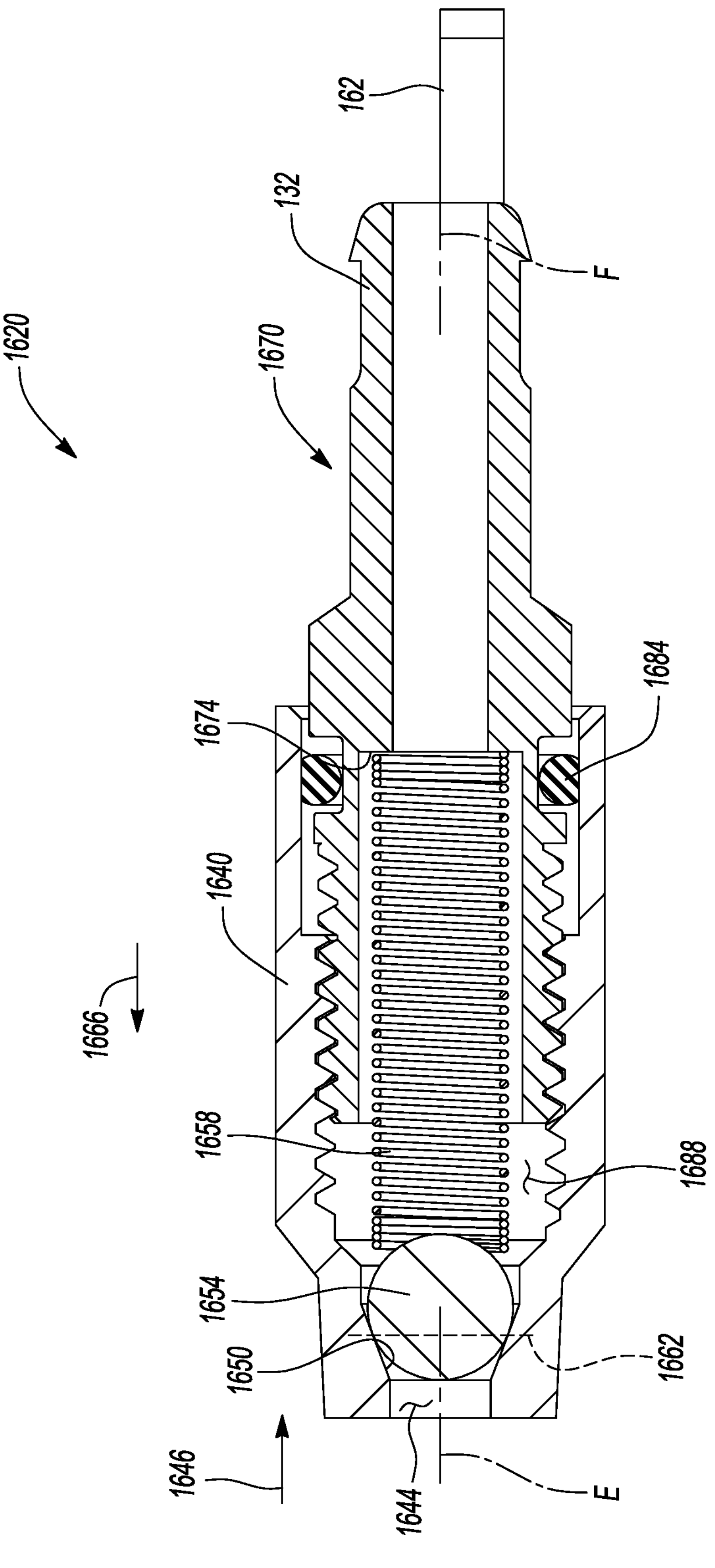
FIG. 26 is a cross-sectional view of the assembled cassette assembly taken along line 26-26 of FIG. 25.

With continuing reference to FIGS. 22-24, and particular reference to FIGS. 25 and 26, the cassette assembly 1620 is discussed and illustrated in greater detail. The cassette assembly 1620 may generally extend along an axis 1629 and have portions aligned relative thereto, as discussed herein. The cassette assembly 1620 may include a cap 1640 which may include an inlet or define an inlet 1644. The inlet 1644 may allow a flow of a fluid generally in the direction of arrow 1646 into the cassette assembly 1620 along the axis 1629. The inlet 1644 may be positioned near or assist in defining a seal or seat 1650.

A sealing member, such as a ball 1654, may be positioned or biased into the seal or seat 1615 with a biasing member 1658. The ball 1654 may seal at a seal position 1662 in the seal 1655 positioning the ball member 1654 within the seal 1650. The biasing member 1658 may generally bias the ball 1654 generally in the direction of an arrow 1666 into the seal 1650 at the seal position 1662. The biasing member 1658 may be positioned between an outlet member 1670 that defines or forms a biasing member contacting surface 1674 to contact the biasing member 1658.

The outlet member 1670 may further define an external thread 1678 that may threadably engage an internal thread 1682. The cap 1640 may be rotatably moved relative to the outlet member 1670 to move the cap 1640 in the direction of either arrow 1646 and/or the arrow 1666. The movement of the cap 1640 relative to the outlet member 1670 may selectively compress the biasing member 1658 to achieve or select a free height and/or spring force or biasing force applied by the biasing member 1658 against the sealing member 1654 and to the seal 1650. Accordingly, a position of the cap 1640 relative to the outlet member 1673 may select an opening pressure force to move the seal member 1654 away from the seal position 1662.

As discussed above, the cassette assembly, such as the cassette assembly 120, may be used to select an opening or cracking pressure of the valve mechanism 1560. A valve mechanism 1680 of the cassette assembly 1620 may include the seal portion 1650, the seal member 1654, and the biasing member 1658. Thus, rotating the cap 1640 relative to the outlet member 1670 may axially position the cap 1640 relative to the outlet member 1670 and select a biasing force applied to the seal member 1654. The biasing force may select or achieve a selected opening force to select an opening pressure or cracking pressure (i.e., threshold pressure) for the sealing member 1654 relative to the cassette assembly 1620 of the valve assembly 1560. A separate rotor, therefore, may not be required to select the cracking pressure.

The cassette assembly 1620 may further include a seal member 1684, such as an O-ring. The seal member 1684 may be positioned between the cap 1640 and the outlet member 1670 to seal a cassette volume 1688 within the cassette assembly 1620. The cassette volume 1688 may be defined between the cap 1640 in outlet member 1670 and may be accessed through the inlet 1644 when the seal end 1640 moves away from the seal position 1662.

Once the cracking pressure is selected and achieved (such as by positioning the cap 1640 relative to the outlet member 1670), the cap 1640 may be fixed relative to the outlet member 1670 in an appropriate manner. As discussed above, various mechanisms may be used to fix the cap assembly or member 1640 to the outlet member 1670 such as adhesives, sonic welding, bonding or the like. In various embodiments, the cap member 1640 may be bonded to the outlet member 1670 in a selected position. Once fixed, therefore, the cassette assembly 1620 may be fixed at the selected position and at the biasing force to achieve a selected inlet pressure of the cassette assembly 1620. The cassette assembly 1620 may then be assembled into the valve assembly 1560, as discussed above and further into the shunt assembly 10.

The valve assembly 1560, as discussed above, may have the cover 1574. The cover may have a maximum external dimension 1690 that is generally less than about 1 millimeter (mm) to about 5 mm less than a minimum external dimension 1690 of the valve assembly 1560 between the position of the maximum dimension and the outlet 1588. Thus, during a possible revisions, the valve assembly 1560, according to various embodiments, may be removed through a single incision.

Figure 27:
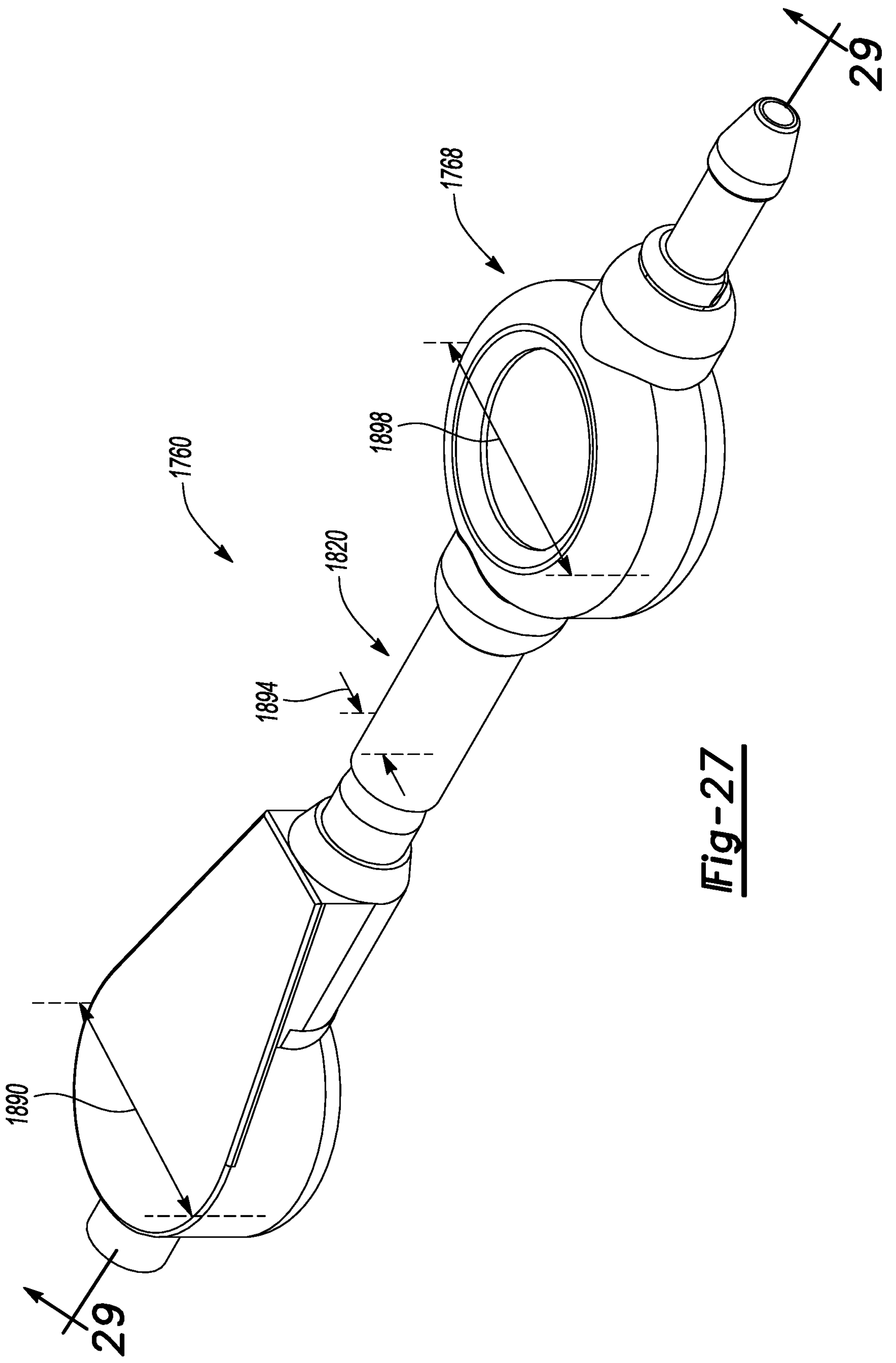
FIG. 27 is perspective view of a valve assembly, according to various embodiments.
Figure 28:
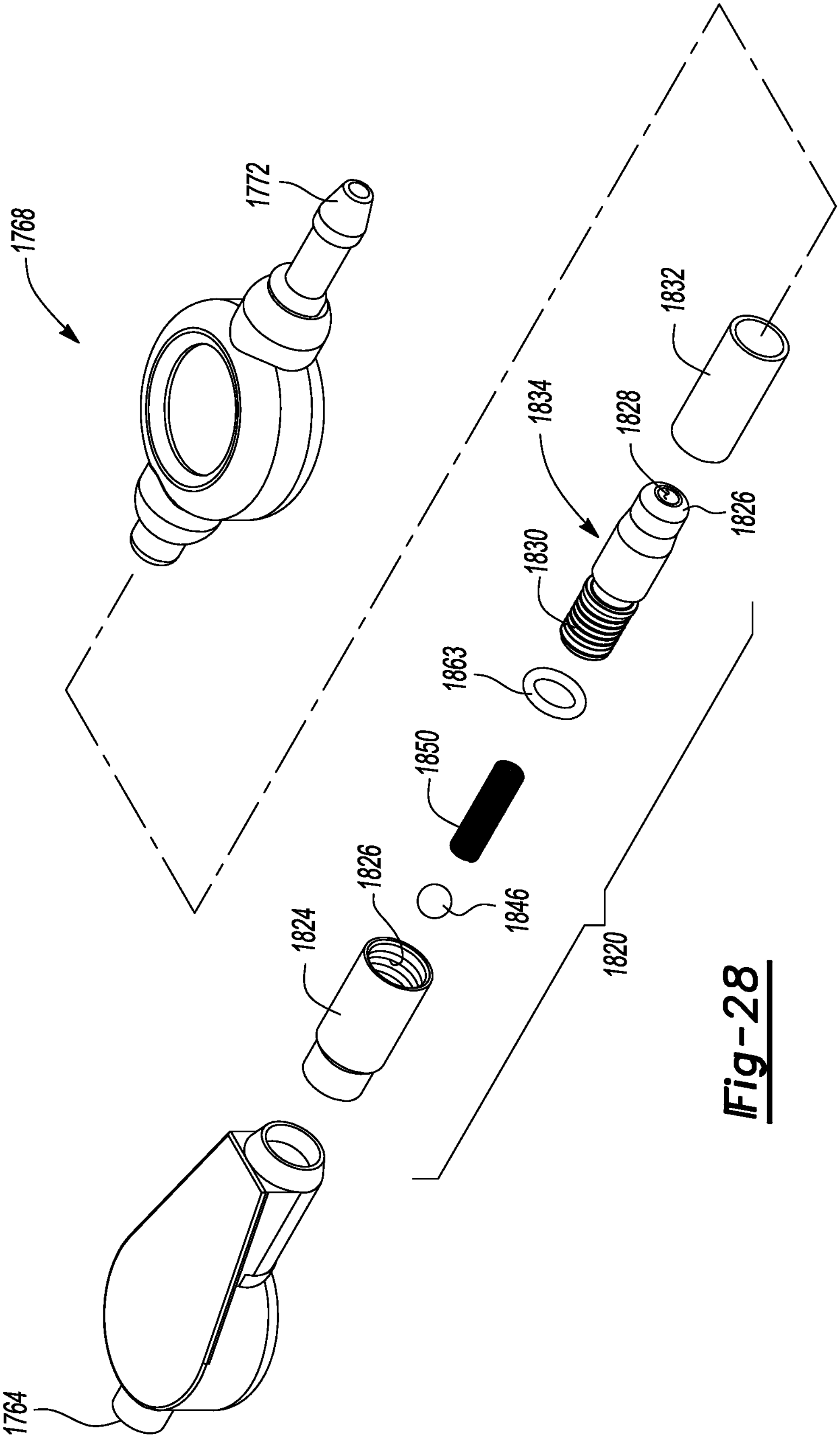
FIG. 28 is an exploded view of a valve and cassette assembly of FIG. 27.
Figure 29:
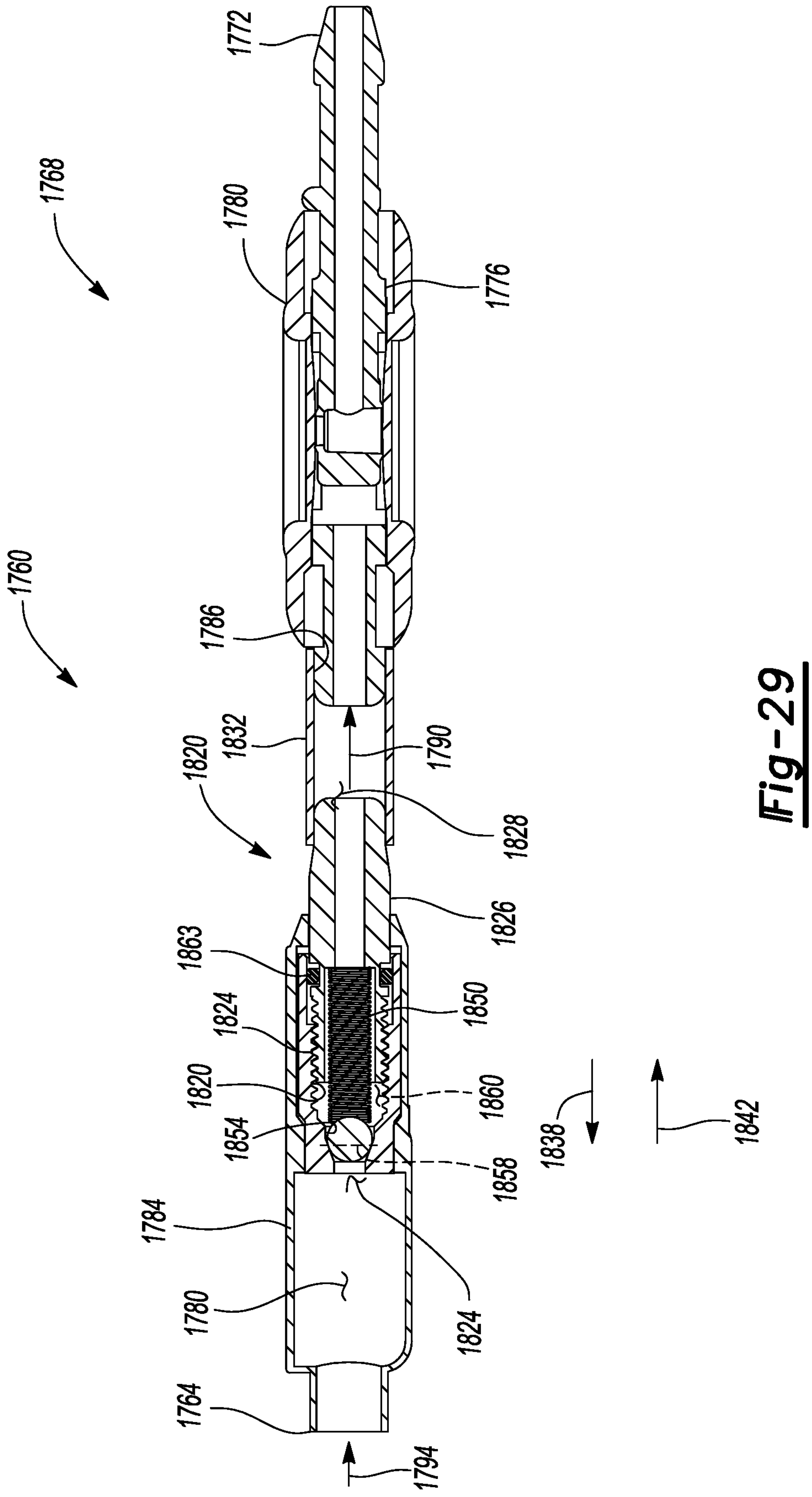
FIG. 29 is an assembled cross-sectional view of the valve assembly of FIG. 27, taken along lines 29-29.

Turning reference to FIGS. 27, 28, and 29, a valve assembly 1760 is illustrated. The valve assembly 1760 may include portions similar to those discussed above, such as in the valve assembly 60. The valve assembly 1760 may include various additional and/or alternative portions as discussed further herein. For example, the valve assembly 1760 may include an inlet 1764 and a flow limiting chamber assembly 1768. The flow limiting chamber assembly 1768 may include an outlet 1772 and a flow limiting chamber portion 1776 and a chamber cover 1780. The valve assembly 1760 may further include a reservoir volume 1780 that is defined or formed by a cover 1784. The cover 1784 may include a material similar to the cover of the dome of the valve assembly 60 as discussed above. Further, the valve assembly 1760 may include an inlet member 1786 into the flow limiting chamber assembly 1768. The inlet 1786 may generally allow a flow of a fluid such as the CSF generally the direction of an arrow 1790. Further, the inlet 1764 may allow a flow of the fluid generally in the direction of arrow 1794. The valve assembly 1760 may further include a cassette assembly 1820. The cassette assembly 1820 may include an inlet 1824 and an outlet member 1826 that forms or defines an outlet 1828. The outlet 1828 and the inlet 1776 may be covered or connected by a connection member 1832. Further, the cassette assembly 1820 may be held or covered by the cover 1784. Thus, the valve assembly 1760 may be substantially in line or elongated valve assembly. The valve assembly 1716 may include portions that are similar to that as discussed above, such as the valve assembly 60. Further, the valve assembly 1760 may include portions that are replaced or alternative to and/or in addition to the valve assembly 60 as discussed above. Nevertheless, the valve assembly 1760 may be included in the shunt assembly as discussed above, and further herein.

The valve 1760 including the cassette assembly 1820 may include portions similar to those to the cassette assemblies discussed above, such as the cassette assembly 120. The cassette assembly 1820 may define or include a valve mechanism that includes a cap 1824 that may define or form an internal thread 1826. The internal thread 1826 may engage in external thread 1830 of an outlet and/or member 1834. The cap 1824 may threadably engage the outlet member 1834 with the thread 1830 to move the cap 1824 generally in the direction of arrow 1838 and/or the direction of 1842. The cassette assembly 1820 may further include a sealing portion or member, such as a ball member 1846. Further, the cassette assembly 1820 may include a biasing member 1850. The biasing member 1850 may hold or bias the sealing member 1846 against a seal or seat 1854 at a seal position 1858. The seal position 1858 may be the position that the ball 1846 seals the cassette assembly 1820, such as a cassette volume 1860. Again, the threaded connection may close the cassette a selected amount and/or a seal member 1863, such as an o-ring, may also be included in the cassette assembly 1820.

The seal member 1846 may be moved away from the seal position 1858 by a force of a fluid, such the CSF, moving generally in the direction of arrow 1842. As discussed above, for example, the cap member 1824 may be moved relative to the outlet member 1834 to select a compression force or length of the biasing member 1850. The biasing member 1850, therefore, may apply a force to the sealing member 1846 to seal the cassette assembly 1820. The position of the cap 1824 relative to the outlet member 1834 with the biasing number 1850 therein may be used to achieve or select an opening or cracking force required to move the seal member 1846 away from the seal position 1858 and allow flow of a fluid, such as the CSF, generally in the direction of arrow 1842 and out to the outlet 1772.

As discussed above, once the selected cracking or opening force is created or achieved, the cap 1824 may be bonded to the outlet member 1834. Bonding of the cap 1824 to the outlet member 1834 may be similar to that as discussed above. The cap 1824 may be fixed to the outlet member 1834 with an intensive, sonic welding, a solvent bonding, or the like. Nevertheless the cassette assembly 1820 may be used to achieve or select a cracking or opening pressure within the valve assembly 1760.

The valve assembly 1760 may include a maximum external dimension 1890 that is greater than about 5 mm than a minimum external dimension 1894. The valve assembly 1760, therefore, may be a "V" shape. The valve assembly may further or alternatively include a third external dimension 1898 that is similar, such as less than 2 mm different, than the maximum external dimension 1890. The valve assembly 1760, therefore, may be a figure "8" or dumbbell shape. The valve assembly 1760 may, therefore, include a small dimension and selected external volume such as for positioning in a small area or subject.

In various embodiments, as discussed above, the valve assembly 60 may include the inlet 1564 and the outlet 1588. The inlet 1564 and the outlet 1588 may be generally aligned and/or coaxial along an axis C (FIG. 23). In various embodiments, the cassette assembly, such as the cassette assembly 1620 may include the valve mechanism or cassette inlet 1644 generally along or having a central axis E and the outlet 132 may extend along an axis F. The axis E may be aligned with the axis F. Thus, all of the axes D, E, and F may be substantially aligned. In various embodiments, the axes D, E, and F, may be generally aligned along the axis 1629.

As discussed above, the shunt assembly 10 may include the valve assembly 60 or a valve assembly according to various embodiments as discussed herein. The valve assembly may include various features or portions including all of those discussed herein, all those alternatively or additionally provided with one another, or according to various embodiments of a cassette assembly as discussed herein. Therefore, the various embodiments discussed herein are not necessarily mutually exclusive, unless so indicated above. Thus the shunt assembly 10 may be provided in the subject to achieve a selected opening pressure or have a selected opening or cracking pressure to allow or select a flow of CSF from the ventricle of the subject. The various valve assemblies may be used to achieve a selected fixed opening pressure once selected during manufacture and/or prior to implementation. In various embodiments, as discussed above, the valve assemblies including the selected cassette assemblies may be used to select an opening or cracking pressure within the valve assembly for the shunt assembly to achieve a selected result and/or treatment for the subject.

As also discussed herein, the biasing member according to various embodiments may be a coil spring, a leaf spring, a compliant or deformable member. Thus, the biasing member may be provided and implemented to provide a selected biasing force on a seal member into a seal portion or seat. The seal member may also include a sphere, curved surface member, conical member or other appropriate shaped member that may seal and unseal from a seal or seat.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A shunt system configured to be placed in a subject, comprising:

an inlet;

an outlet;

a reservoir in a fluid flow path from the inlet to the outlet, wherein a fluid is operable to flow in the inlet, through the reservoir, and out the outlet; and a valve mechanism positioned between the inlet and the outlet to control a flow from the inlet to the outlet at a selected threshold pressure, wherein the valve mechanism comprises, a housing having at least one adjustment area and an internal wall that defines an internal polygon, an adjustment member having (i) a first side and an adjustment portion extending from the first side, wherein the adjustment portion is configured to engage the at least one adjustment area, (ii) a second side that defines a biasing member seat, wherein the second side is opposite the first side, and (iii) an outer wall that extends between the first side and the second side, wherein the outer wall defines an external polygon that is complementary to the internal polygon, wherein the outer wall of the adjustment member includes a projection extending from the outer wall, and wherein the projection is configured to be held in a selected, fixed position within one of a plurality of depressions defined in an inner wall of the internal polygon by virtue of the complementary geometry of the inner wall and the outer wall, a seal member configured to seal the shunt system when positioned in a seal position, and a biasing member configured to bias the seal member in the seal position with a selected biasing force, wherein the biasing force is selected at least in part by the position of the adjustment member relative to the seal position, wherein the interaction of the external polygon of the outer wall and the internal polygon of the inner wall is configured to mechanically complement one another and rotationally fix the adjustment member in the selected, fixed position within the housing eliminating the need for a separately actuatable positive locking tool.

2. The shunt system of claim 1, wherein the first side and the second side extend continuously from edge to edge of the adjustment member.

3. The shunt system of claim 1, wherein the depression includes a plurality of depressions, and wherein the projection is configured to be selectively held in each depression of the plurality of depressions by the complementary internal and external geometry of the respective inner wall and the outer wall, the geometry of both the outer wall and the inner wall also being symmetrical allowing the outer wall to be selectively rotated and locked relative to the inner wall to adjust the bias of the biasing member.

4. The shunt system of claim 1, wherein the at least one adjustment area includes at least an outer adjustment area and an inner adjustment area.

5. The shunt system of claim 1, wherein the adjustment area includes a first portion and a second portion;

wherein the adjustment portion of the adjustment member is configured to engage both the first portion and the second portion;

wherein the adjustment member is moved closer to the seal position when engaged on the second position then the first position.

6. The shunt system of claim 5, wherein the adjustment area further includes at least a third portion, a fourth portion, and a fifth portion;

wherein the adjustment portion of the adjustment member is configured to be positioned to engage at least one of the first portion, the second portion, the third portion, the fourth portion, or the fifth portion to set a distance of the biasing member seat relative to the seal position.

7. The shunt system of claim 6, wherein a force to open the seal member from the seal position is set by the relative position of the biasing member seat relative to the seal position.

8. The shunt system of claim 6, wherein each of the first portion, the second portion, the third portion, the fourth portion, or the fifth portion has a top surface that is distinct distance from the seal position.

9. The shunt system of claim 1, further comprising:

a top member configured to cover a selected portion of the housing; and a seal portion that defines the seal position relative to the top member;

wherein the top member defines a valve mechanism inlet.

10. The shunt system of claim 1, wherein the adjustment member includes a spring engaging surface and bottom surface on opposing sides thereof, the bottom surface including an outer foot projection extending therefrom and an inner foot projection extending therefrom.

11. The shunt system of claim 10, wherein the outer foot projection is configured to contact an outer selected region defined in the housing and the inner foot projection is configured to contact an inner selected region defined in the housing.

12. The shunt system of claim 11, wherein the outer selected region includes a plurality of outer portions defined thereon, each outer portion of the plurality of outer portions having a different height and wherein the inner selected region includes a plurality of inner portions defined thereon, each inner portion of the plurality of inner portions having a different height.

13. The shunt system of claim 12, wherein rotation of the adjustment member relative to the housing engages the inner foot projection with one of the plurality of inner portions and engages the outer foot projection with one of the plurality of outer portions which, in turn, varies the biasing force on the biasing member.

* * * * *